(12) United States Patent
Zhu et al.

(10) Patent No.: US 6,537,998 B1
(45) Date of Patent: Mar. 25, 2003

(54) GONADOTROPIN-RELEASING HORMONE RECEPTOR ANTAGONISTS AND METHODS RELATING THERETO

(75) Inventors: Yun-Fei Zhu, San Diego, CA (US); Timothy D. Gross, San Diego, CA (US); Yinghong Gao, San Diego, CA (US); Patrick J. Connors, Jr., San Diego, CA (US); Zhiqiang Guo, San Diego, CA (US); Chen Chen, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 09/688,774

(22) Filed: Oct. 16, 2000

Related U.S. Application Data

(60) Provisional application No. 60/304,171, filed on Oct. 15, 1999.

(51) Int. Cl.$^7$ .................. C07D 487/04; A61K 31/505; A61P 5/02
(52) U.S. Cl. .................. 514/259.5; 544/263; 544/281; 544/282
(58) Field of Search ................. 544/263, 281, 544/282; 514/259.5

(56) References Cited

U.S. PATENT DOCUMENTS

| 5,780,437 A | 7/1998 | Goulet et al. ................. 514/19 |
| 5,849,764 A | 12/1998 | Goulet et al. ................. 514/337 |

FOREIGN PATENT DOCUMENTS

| WO | WO 96/38438 | 12/1996 |
| WO | WO 97/14682 | 4/1997 |
| WO | WO 97/14697 | 4/1997 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 97/44037 | 11/1997 |
| WO | WO 97/44041 | 11/1997 |
| WO | WO 97/44321 | 11/1997 |
| WO | WO 97/44339 | 11/1997 |
| WO | WO 98/55116 | 12/1998 |
| WO | WO 98/55119 | 12/1998 |
| WO | WO 98/55470 | 12/1998 |
| WO | WO 98/55479 | 12/1998 |
| WO | WO 99/09033 | 2/1999 |
| WO | WO 99/33831 | 7/1999 |
| WO | WO 99/33831 A1 * | 7/1999 |
| WO | WO 99/44339 | 9/1999 |
| WO | WO 99/51232 | 10/1999 |

OTHER PUBLICATIONS

Patterson, Austin M et al, "The Ring Index, 2$^{nd}$ Ed", American Chemical Society, 1960, Washington, DC, pp. 144, 156, and 165.*
Draetta, G. and Pagano, M. in "Annual Reports in Medicinal Chemistry, vol. 31", 1996, Academic Press, San Diego, p241–246.*
Hallegua, D. et al, Lupus, 2000, 9, 241–251.*
Khamashta, M.A. et al, Expert. Opin. Investig. Drugs, 2000, 9(7), 1581–93.*
Cho et al., "Discovery of a Novel, Potent, and Orally Active Nonpeptide Antagonist of the Human Luteinizing Hormone–Releasing Hormone (LHRH) Receptor," *J. Med. Chem.* 41(22): 4190–4195, 1998.
Koerber et al., "Consensus Bioactive Conformation of Cyclic GnRH Antagonists Defined by NMR and Molecular Modeling," *J. Med. Chem.* 43(5):819–828, 2000.

* cited by examiner

*Primary Examiner*—Bruck Kifle
*Assistant Examiner*—Thomas C McKenzie
(74) *Attorney, Agent, or Firm*—Seed Intellectual Property Law Group PLLC

(57) ABSTRACT

GnRH receptor antagonists are disclosed which have utility in the treatment of a variety of sex-hormone related conditions in both men and women. The compounds of this invention have the structure:

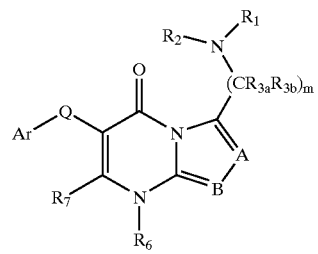

wherein Ar, A, B, Q, $R_1$, $R_2$, $R_{3a}$, $R_{3b}$, $R_6$, $R_7$ and m are as defined herein, including stereoisomers, prodrugs and pharmaceutical acceptable salts thereof. Also disclosed are compositions containing a compound of this invention in combination with a pharmaceutically acceptable carrier, as well as methods relating to the use thereof for antagonizing gonadotropin-releasing hormone in a subject in need thereof.

30 Claims, No Drawings

GONADOTROPIN-RELEASING HORMONE RECEPTOR ANTAGONISTS AND METHODS RELATING THERETO

CROSS REFERENCE TO RELATED APPLICATION

This invention claims the benefit of U.S. Provisional Application No. 60/304,171 filed Oct. 15, 1999; which application was originally filed as U.S. application Ser. No. 09/418,768 filed Oct. 15, 1999 and converted to provisional application No. 60/304,171 by petition mailed Oct. 16, 2000.

TECHNICAL FIELD

This invention relates generally to gonadotropin-releasing hormone (GnRH) receptor antagonists, and to methods of treating disorders by administration of such antagonists to a warm-blooded animal in need thereof.

BACKGROUND OF THE INVENTION

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-$NH_2$) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostate cancer, breast cancer, endometriosis, uterine leiomyoma, and precocious puberty. For example, peptidic GnRH agonists, such as leuprorelin (pGlu-His-Trp-Ser-Tyr-D-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2–3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. For example, Cho et al. (*J. Med. Chem.* 41:4190–4195, 1998) discloses thieno[2,3-b]pyridin-4-ones for use as GnRH receptor antagonists; U.S. Pat. Nos. 5,780, 437 and 5,849,764 teach substituted indoles as GnRH receptor antagonists (as do published PCTs WO 97/21704, 98/55479, 98/55470, 98/55116, 98/55119, 97/21707, 97/21703 and 97/21435); published PCT WO 96/38438 discloses tricyclic diazepines as GnRH receptor antagonists; published PCTs WO97/14682, 97/14697 and 99/09033 disclose quinoline and thienopyridine derivatives as GnRH antagonists; published PCTs WO 97/44037, 97/44041, 97/44321 and 97/44339 teach substituted quinolin-2-ones as GnRH receptor antagonists; and published PCT WO 99/33831 discloses certain phenyl-substituted fused nitrogen-containing bicyclic compounds as GnRH receptor antagonists.

While significant strides have been made in this field, there remains a need in the art for effective small molecule GnRH receptor antagonists. There is also a need for pharmaceutical compositions containing such GnRH receptor antagonists, as well as methods relating to the use thereof to treat, for example, sex-hormone related conditions. The present invention fulfills these needs, and provides other related advantages.

SUMMARY OF THE INVENTION

In brief, this invention is generally directed to gonadotropin-releasing hormone (GnRH) receptor antagonists, as well as to methods for their preparation and use, and to pharmaceutical compositions containing the same. More specifically, the GnRH receptor antagonists of this invention are compounds having the following general structure (I):

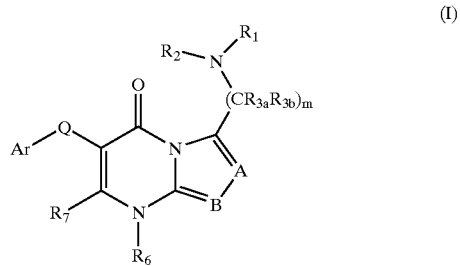

including stereoisomers, prodrugs and pharmaceutically acceptable salts thereof, wherein Ar, A, B, Q, $R_1$, $R_2$, $R_{3a}$, $R_{3b}$, $R_6$, $R_7$ and m are as defined below.

The GnRH receptor antagonists of this invention have utility over a wide range of therapeutic applications, and may be used to treat a variety of sex-hormone related conditions in both men and women, as well as a mammal in general (also referred to herein as a "subject"). For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization). The compounds of this invention are also useful as an adjunct to treatment of growth hormone deficiency and short stature, and for the treatment of systemic lupus erythematosis. The compounds are also useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. In addition, the compounds may be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

The methods of this invention include administering an effective amount of a GnRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as gonadotropin-releasing hormone (GnRH) receptor antagonists. The compounds of this invention have the following structure (I):

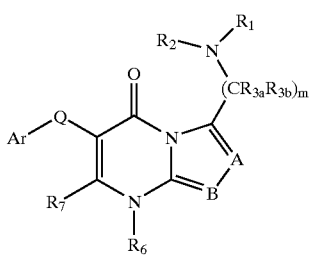

including stereoisomers, prodrugs and pharmaceutically acceptable salts thereof, wherein:

A is independently selected from N or $CR_4$;

B is independently selected from N or $CR_5$;

Q is a direct bond or —$(CR_{8a}R_{8b})_r$—Z—$(CR_{10a}R_{10b})_s$—;

m, r and s are the same or different and selected from an integer from 0 to 6;

Z is a direct bond or —O—, —S—, —$NR_9$—, —SO—, —$SO_2$—, —$OSO_2$—, —$SO_2O$—, —$SO_2NR_9$—, —$NR_9SO_2$—, —CO—, —COO—, —OCO—, —$CONR_9$—, —$NR_9CO$—, —$NR_9CONR_{9a}$—, —$OCONR_9$— or —$NR_9COO$—;

$R_1$ is hydrogen, alkyl, substituted alkyl, aryl, substituted aryl, arylalkyl, substituted arylalkyl, heteroaryl, substituted heteroaryl, heteroarylalkyl, substituted heteroarylalkyl, —$C(R_{1a})(=NR_{1b})$, or —$C(NR_{1a}R_{1c})(=NR_{1b})$;

$R_2$ is hydrogen, alkyl or substituted alkyl;

or $R_1$ and $R_2$ taken together with the nitrogen atom to which they are attached form a heterocycle ring or a substituted heterocycle ring;

$R_{3a}$ and $R_{3b}$ are independently selected from hydrogen, alkyl, substituted alkyl, aryl, substituted aryl, arylalkyl, heterocycle, heterocyclealkyl, hydroxy, alkoxy, alkylthio, alkylamino, $CONR_{14}R_{15}$, or —$COOR_{14}$;

or $R_{3a}$ and $R_{3b}$ taken together with the carbon atom to which they are attached form a 3–6 membered homocyclic ring, substituted homocyclic ring, heterocyclic ring or substituted heterocyclic ring;

or $R_{3a}$ and $R_{3b}$ taken together form =$NR_{3c}$;

$R_4$ is hydrogen, halogen, cyano, nitro, alkyl, substituted alkyl, arylalkyl, substituted arylalkyl, heterocyclealkyl, substituted heterocyclealkyl, —$COR_{11}$, —$COOR_{11}$, —$CONR_{12}R_{13}$, —$OR_{11}$, —$OCOR_{11}$, —$OSO_2R_{11}$, —$SR_{11}$, —$SO_2R_{11}$, —$NR_{12}R_{13}$, —$NR_{11}COR_{12}$, —$NR_{11}CONR_{12}R_{13}$, —$NR_{11}SO_2R_{12}$ or —$NR_{11}SO_2NR_{12}R_{13}$; or $R_4$ and $R_1$, together with the atoms to which they are attached, form a 5–7 member heterocyclic ring or substituted heterocyclic ring;

or $R_4$ and $R_{3a}$, together with the atoms to which they are attached, form a 5–7 membered homocyclic ring, substituted homocyclic ring, heterocyclic ring or substituted heterocyclic ring;

$R_5$ is hydrogen, halogen, lower alkyl, arylalkyl, alkoxy, alkylthio, alkylamino, cyano or nitro;

$R_6$ is hydrogen, alkyl, substituted alkyl, aryl, substituted aryl, arylalkyl, substituted arylalkyl, heteroaryl, substituted heteroaryl, heteroarylalkyl or substituted heteroarylalkyl;

$R_7$ is hydrogen, halogen, cyano, alkyl, substituted alkyl, alkoxy, alkylthio, alkylsulfonyl or alkylamino;

Ar is aryl, heteroaryl, substituted aryl or substituted heteroaryl; and $R_{1a}$, $R_{1b}$, $R_{1c}$, $R_{3c}$, $R_{8a}$, $R_{8b}$, $R_9$, $R_{9a}$, $R_{10a}$, $R_{10b}$, $R_{11}$, $R_{12}$, $R_{13}$, $R_{14}$ and $R_{15}$ are the same or different and at each occurrence independently hydrogen, acyl, alkyl, substituted alkyl, aryl, substituted aryl, arylalkyl, substituted arylalkyl, heterocycle, substituted heterocycle, heterocyclealkyl or substituted heterocyclealkyl;

or $R_{1a}$ and $R_{1b}$, $R_{8a}$ and $R_{8b}$, $R_{10a}$ and $R_{10b}$, or $R_{12}$ and $R_{13}$ taken together with the atom or atoms to which they are attached form a homocyclic ring, substituted homocyclic ring, heterocyclic ring or substituted heterocyclic ring.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —$(CH_2)_2$phenyl, —$(CH_2)_3$phenyl, —$CH(phenyl)_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocycle ring") means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quatemized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Homocycle" means a saturated or unsaturated (but not aromatic) carbocyclic ring containing from 5–7 carbon atoms, such as cyclopentane, cyclohexane, cycloheptane, cyclohexene, and the like.

The term "substituted" as used herein means any of the above groups (i.e., alkyl, aryl, arylalkyl, heteroaryl, heteroarylalkyl, homocycle, heterocycle and heterocyclealkyl) wherein at least one hydrogen atom is replaced with a substituent. In the case of a keto substituent ("—C(=O)—") two hydrogen atoms are replaced. When substituted, "substituents" within the context of this invention include halogen, hydroxy, cyano, nitro, amino, alkylamino, dialkylamino, alkyl, alkoxy, alkylthio, haloalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$NR$_b$, —NR$_a$C(=O)OR$_b$ —NR$_a$SO$_2$R$_b$, —C(=O)R$_a$ —C(=O)OR$_a$, —C(=O)NR$_a$R$_b$, —OC(=O)NR$_a$R$_b$, —SH, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

In one embodiment of this invention, Q is a direct bond and representative GnRH receptor antagonists of this invention include compounds having the following structure (II):

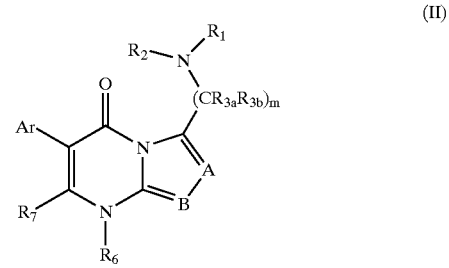

(II)

In a further embodiment of structure (II), Ar is phenyl, substituted phenyl, heteroaryl or substituted heteroaryl.

In another embodiment, Q is —(CR$_{8a}$R$_{8b}$)$_r$—Z—(CR$_{10a}$R$_{10b}$)$_s$—, r and s are both zero, and representative GnRH receptor antagonists of this invention include compounds having the following structure (III):

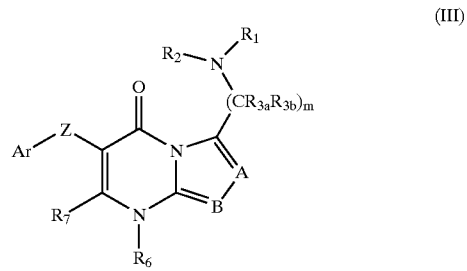

(III)

In another embodiment of structures (II), A is CR$_4$ and B is N, as represented by the following structures (IV):

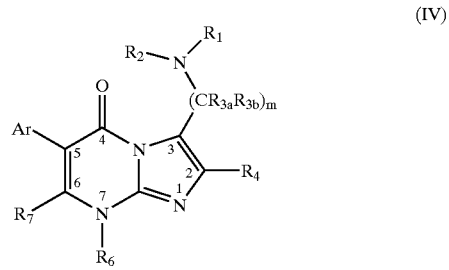

(IV)

Similarly, in another embodiment of structures (II), A is CR$_4$ and B is CR$_5$, as represented by the following structure (V):

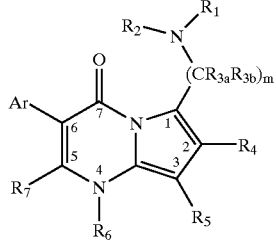

(V)

In still further embodiments of structure (II), A is N and B is $R_5$ or both A and B are N, as represented by the following structures (VI) and (VII), respectively:

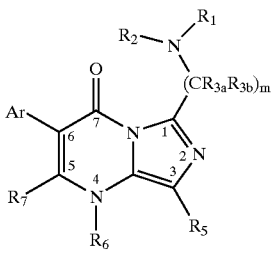

(VI)

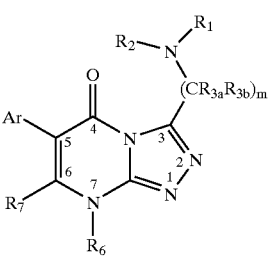

(VII)

In yet further embodiments of structure (I) of this invention, Q is a direct bond, $R_6$ is benzyl (substituted or unsubstituted), A is $CR_4$ and B is N or $CR_5$, as represented by the following structures (VIII) and (IX), respectively (wherein X represents one or more optional substituents as defined above):

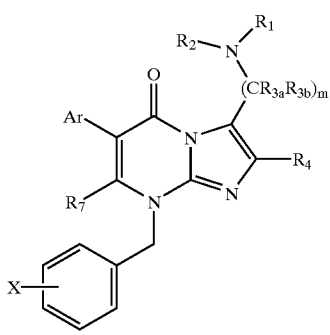

(VIII)

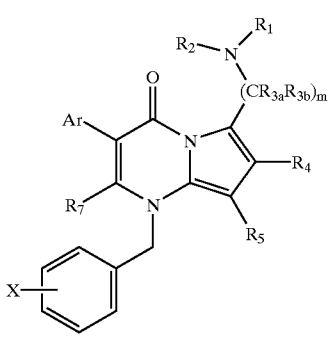

(IX)

In a more specific embodiment of structures (VIII) and (IX), m is 1 and both $R_{3a}$ and $R_{3b}$ are hydrogen, as represented by the following structures (X) and (XI):

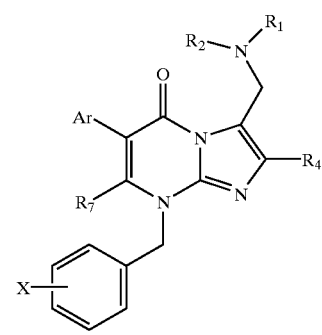

(X)

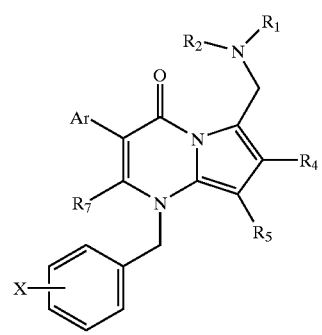

(XI)

In still more specific embodiments, $R_7$ in structures (X) and (XI) is methyl, as represented by the following structures (XII) and (XIII), respectively:

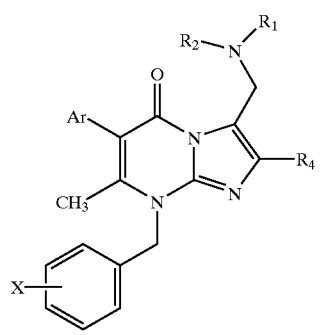

(XII)

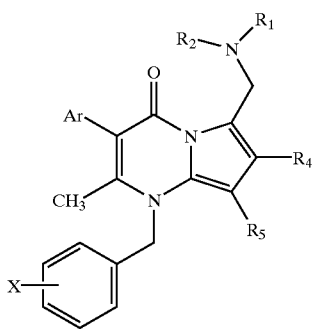

(XIII)

One class of representative compounds having structures (XII) or (XIII) include those compounds wherein Ar is aryl, substituted aryl, heteroaryl or substituted heteroaryl, such as substituted or unsubstituted phenyl, pyridyl, pyrimidinyl, and the like.

The compounds of the present invention may be prepared by known organic synthesis techniques, including the methods described in more detail in the Examples. However in general, the compounds of structure (I) above may be made by the following Reaction Schemes. Specifically, compounds wherein A is $CR_4$ and B is N may be made by Reaction Scheme A, compounds wherein A is $CR_4$ and B is $CR_5$ may be made by Reaction Scheme B, compounds wherein A is N and B is $CR_5$ may be made by Reaction Scheme C, and compounds wherein A is N and B is N may be made by Reaction Scheme D. All substituents in the following Reaction Schemes are as defined above unless indicated otherwise. To this end, $R_3$ and $R_8$ in the following Reaction Schemes are the same or different and independently hydrogen, a substituent as defined above, or the moiety —Q—Ar.

Reaction Scheme A

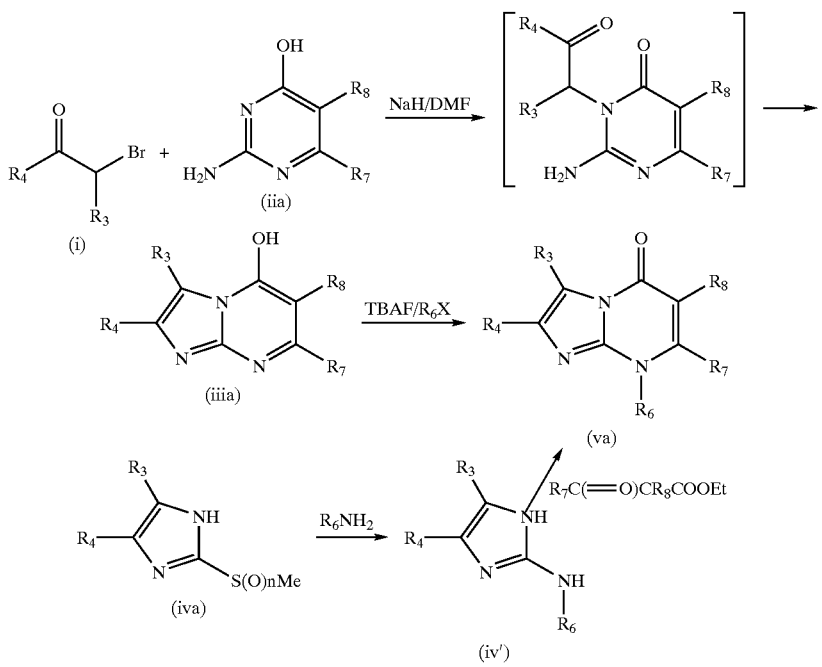

Cyclization of α-bromocarbonyl or α-bromocarboxylate (i) with 2-aminopyrimid-4-one (iia) in the presence of a base such as sodium hydride, tetrabutylammonium fluoride, potassium carbonate in an inert solvent such as DME, dimethylformamide, ethanol at a temperature of 25–100° C. for a period of 12–24 hours gives the imidazolo[1,2-a] pyrimidone (iiia). Compound (iiia) can be modified by alkylation with an alkyl halide in the presence of a base such as TBAF, sodium hydride or silver oxide in an inert solvent such as DME, THF or DMF at a temperature of 0–100° C. for a period of 1–24 hours to give the 7-alkylated imidazolo [1,2-a]pyrimid-4-one (va).

Alternatively, the imidazolopyrimidone (va) can be synthesized from imidazole (iva). Reaction of compound (iva) with a primary amine with or without a solvent such as DMF, DMSO, toluene or glycol at a temperature of 25–180° C. for a period of 2–24 hours gives the 2-aminoimidazole (iv'), which reacts with a acetoacetate derivative in a solvent such as dioxane, ethanol or DMF at a temperature of 25–120° C. for a period of 2–24 hours gives the desired-compound (va).

Reaction Scheme B

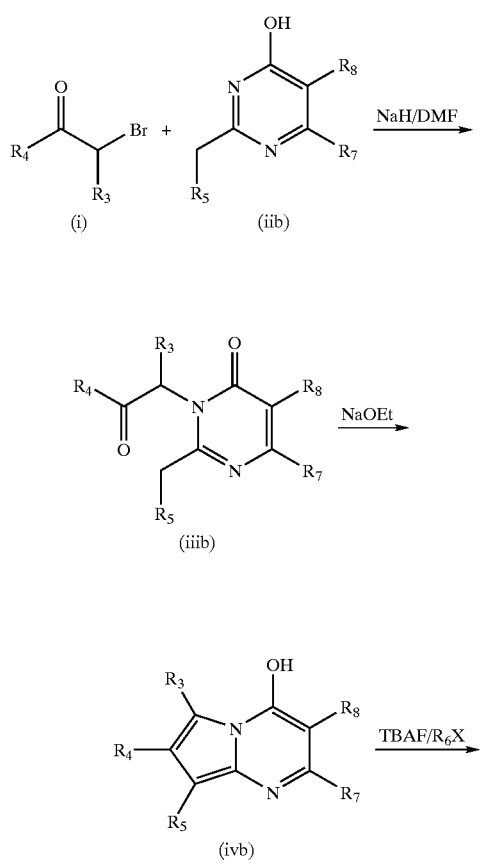

Reaction Scheme C

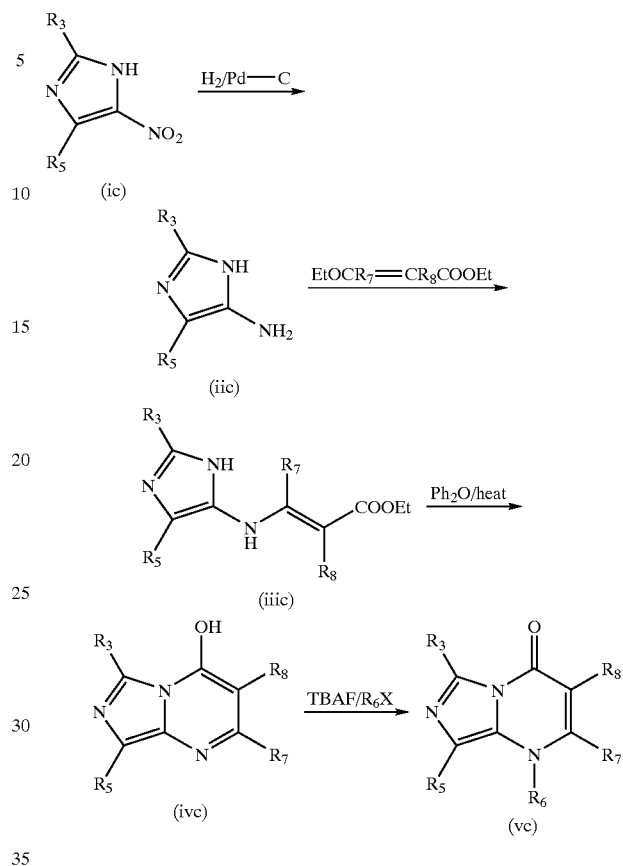

Reduction of the 4-nitroimidazole (ic) with hydrogenation catalyzed by a catalyst such as palladium on carbon, under hydrogen atmosphere, in a solvent such as methanol, acetic acid or ethyl acetate at room temperature for a period of 1–16 hours gives the 4-aminoimidazole (iic). Reaction of compound (iic) with beta-ethoxyacrylate in a solvent such as benzene or methanol with or without a catalyst such as toluenesulfonic acid at a temperature of 25–100° C. for a period of 1–16 hours gives the enamine (iiic). When the compound (iiic) is heated at a temperature of 200–280° C. in a solvent such as phenyl ether for a period of 0.25 to 2 hours the cyclized product (ivc) is obtained. Compound (ivc) can be modified by alkylation in the presence of a base such as sodium hydride, TBAF or potassium carbonate in an inert solvent such as THF, DME or DMF at a temperature of 25–100° C. for a period of 1–16 hours to give compound (vc).

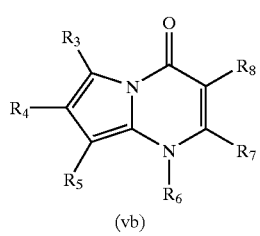

Reaction of α-bromocarbonyl (i) with 4-hydroxypyridine (iib) in the presence of a base such as sodium hydride, TBAF, or potassium carbonate in an inert solvent such as DMF, THF or ethanol at a temperature of 25–100° C. for a period of 1–24 hours gives the N-alkylated pyrimidone (iiib). Compound (iiib) can be cyclized in the presence of a base such as sodium ethoxide, sodium methoxide or potassium t-butoxide in an inert solvent such as ethanol, THF or DMF at a temperature of 25–100° C. for a period of 0.5 to 16 hours gives the pyrrolo[1,2-a]pyrimidone (ivb). Alkylation of compound (ivb) can be accomplished with an alkyl halide in the presence of a base such as sodium hydride, TBAF or potassium carbonate at a temperature of 25–100° C. for a period of 1–24 hours give the alkylated compound (vb).

Reaction Scheme D

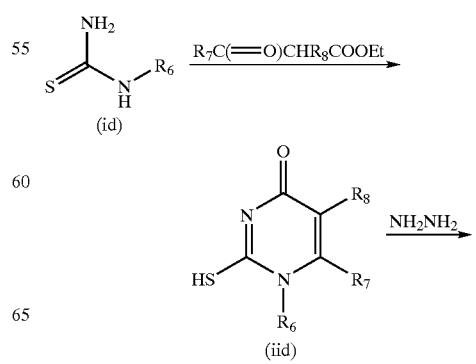

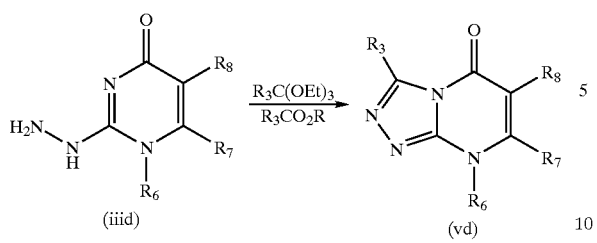
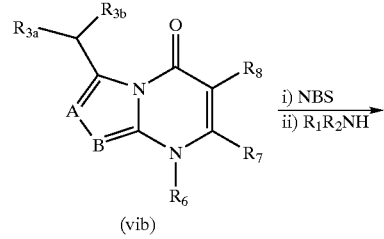
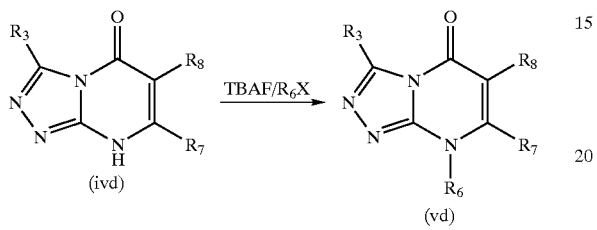
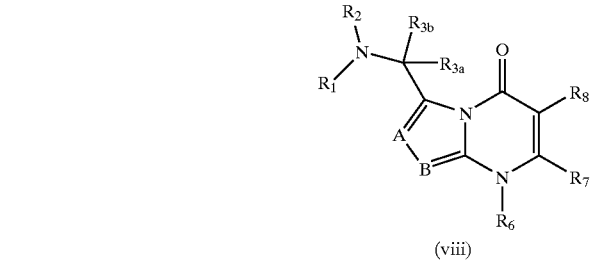

Cyclization of thiourea (1d) with an acetoacetate derivative in the presence of a base such as sodium methoxide or potassium t-butoxide in an inert solvent such as methanol, ethanol at a temperature of 25–120° C. for a period of 2–24 hours gives the pyrimidone (iid) as one of the two isomers. Reaction of compound (iid) with hydrazine in an appropriate solvent such as ethanol or water at a temperature of 25–100° C. for a period of 1–24 hours give the hydazinopyrimidine (iiid), which is cyclized upon treatment of triethoxyalkane or a carboxylic acid derivative at a temperature of 25–120° C. for a period of 2–24 hours to give the 1,2,4-triazolo[1,2-a]pyrimidone (vd).

Alternatively, compound (vd) can be obtained by alkylation of compound (ivd) with an alkyl halide in the presence of a base such as sodium hydride, TBAF, potassium carbonate at a temperature of 25–100° C. for a period of 1–24 hours.

The amino compound (vii) can be prepared by treatment of the starting material (via) with a secondary amine and an aldehyde such as formaldehyde or acetaldehyde in an appropriate solvent such as ethanol, dioxane or acetic acid at a temperature of 25–100° C. for a period of 1–24 hours.

The pyrimidone (vib) can be modified by treatment with a halogenating reagent such as N-bromosuccinamide in an inert solvent such as tetrachloromethane or DMF at a temperature of 50–100° C. for a period of 2–16 hours to give a halide compound, which reacts with a primary or secondary amine with or without an amine base such as triethylamine, diisopropylethylamine or pyridine in an inert solvent such as chloroform, tetrachloromethane or tetrahydrofuran at a temperature of 25–80° C. for a period of 1–16 hours to give the amino analog (viii).

Reaction Scheme F

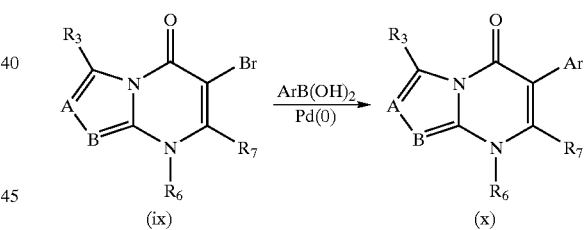

Reaction Scheme E

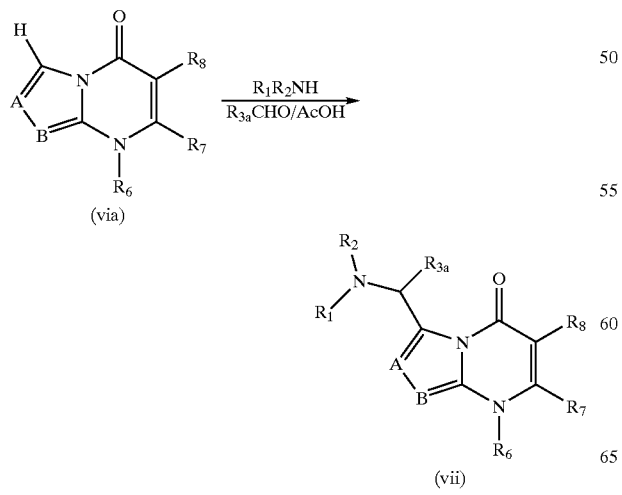
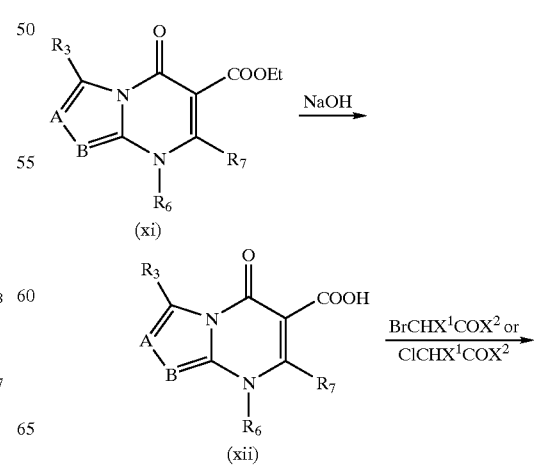

-continued

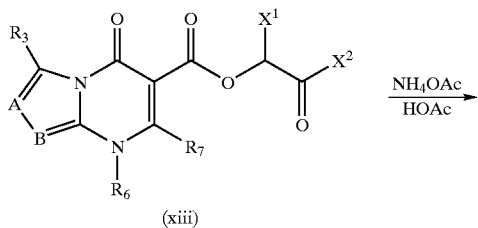

(xiii)

The bromopyrimidone (ix) can be converted to the corresponding aryl (Ar=phenyl or substituted phenyl) or heteroaryl (heterocyclic aromatic ring with or without substituents) compound (x) by a palladium-catalyzed cross coupling reaction of compound (ix) with an organoboronic acid in the presence of a base such as sodium carbonate, cesium fluoride, or sodium acetate in an inert solvent such as benzene, ethanol, water or mixture thereof at a temperature of 25–120° C. for a period of 1–72 hours. Alternatively, heteroaryl compound such as oxazole (xiv) can be prepared by a cyclization of an ester (xiii) with an ammonium moiety such as ammonium acetate in an appropriate solvent such as acetic acid at a temperature of 25–120° C. for 1–24 hours. The ester (xiii) can be synthesized from alkylation of an acid (xii) with a alpha-bromoketone in the presence of a base such as potassium carbonate or triethylamine in an inert solvent such as DMF at a temperature of 25–100° C. for a period of 1–24 hours (wherein $X^1$ and $X^2$ are substituents as defined herein).

Reaction Scheme G

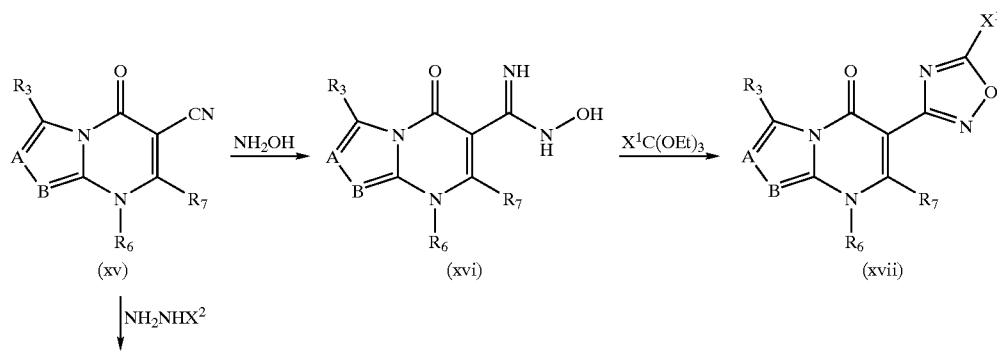

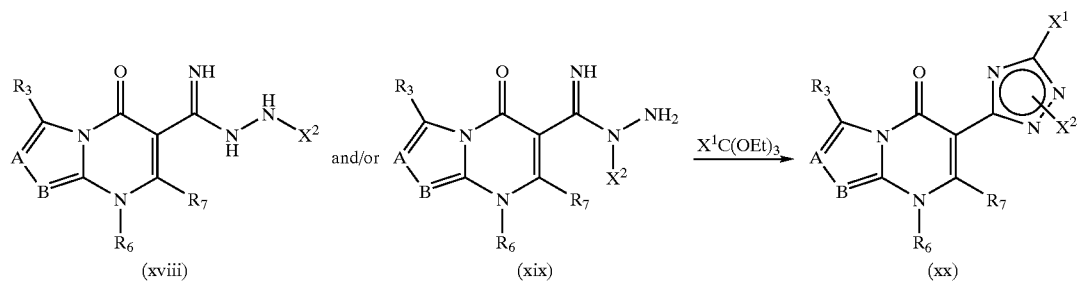

-continued

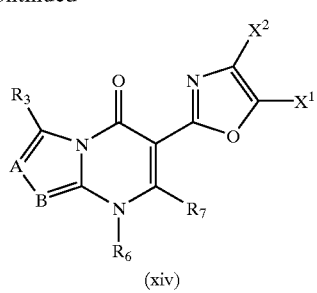

(xiv)

Cyano compound (xv) can be converted to the corresponding heteroaryl analogs such as oxodiazole or triazole. Reaction of compound (xv) with hydroxylamine in a solvent such as methanol, ethanol, water, dioxane or the mixture thereof at a temperature of 25–120° C. for a period of 1–24 hours gives the N-hydroxylamidine (xvi), which is treated with triethoxyalkane with or without a solvent such as ethanol, dioxane or an appropriate carboxylic acid at a temperature of 25–120° C. for a period of 1–24 hours to give the 1,2,3-oxodiazole (xvii) (wherein $X^1$ is a substituent as defined herein). Reaction of (xv) with hydrazine, including alkylhydrazine and arylhydrazine in an appropriate solvent such as ethanol, dioxane, water or a mixture thereof for a period of 1–24 hours gives N-aminoamidine (xviii) or (xix) (wherein $X^1$ is a substituent as defined herein), which is converted to the corresponding 1,2,3-triazole (xx) by reaction with triethoxyalkane (wherein $X^2$ is a substituent as defined herein) with or without a solvent such as dioxane, Reaction Scheme H

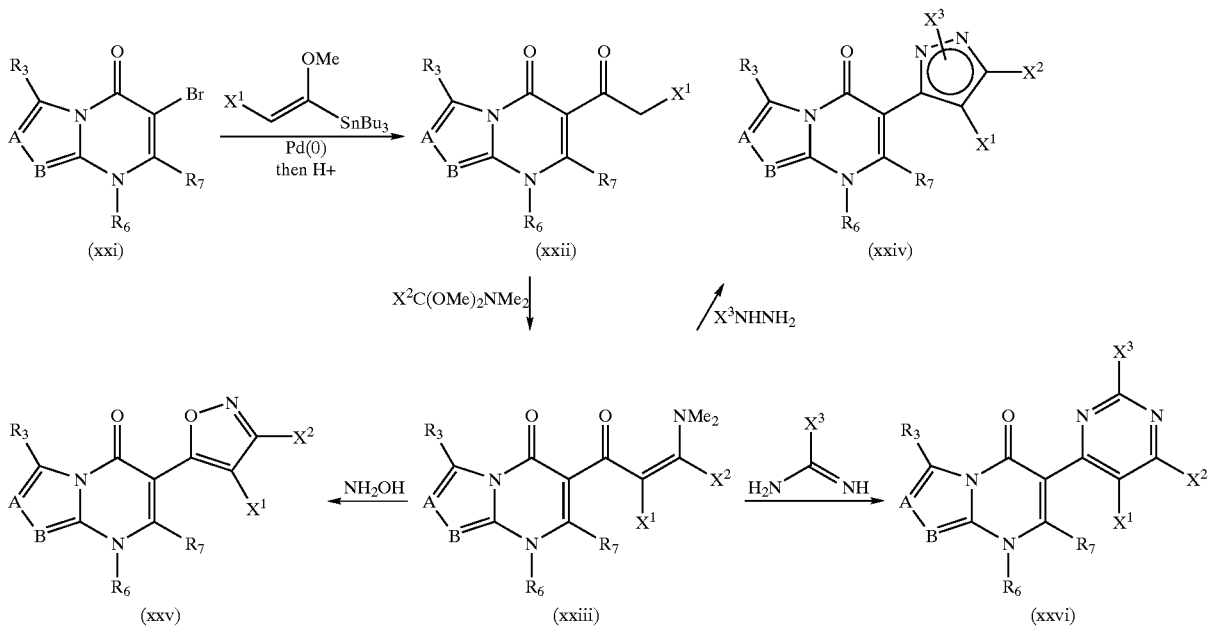

The bromo pyrimidone (xxi) can be modified by a palladium catalyzed cross coupling with a vinyltin in a solvent such as THF, toluene or DMF at a temperature of 25–120° C. for a period of 1–24 hours to give the ketone (xxii) (wherein $X^1$ is a substituent). Condensation of the ketone (xxii) with triethoxyalkane or dimethoxydimethylaminoalkane with or without a solvent such as toluene, dioxane or DMF at a temperature of 25–120° C. for a period of 1–24 hours gives the α,β-unsaturated ketone (xxiii) (wherein $X^2$ is a substituent). Cyclization of compound (xxiii) with hydrazine including alkylhydrazine and arylhydrazine in a solvent such as ethanol, dioxane, water or a mixture thereof at a temperature of 25–120° C. for a period of 1–24 hours gives pyrazole (xxiv) (wherein $X^3$ is a substituent). Cyclization of compound (xxiii) with hydroxylamine in a solvent such as ethanol, dioxane, water or a mixture thereof at a temperature of 25–120° C. for a period of 1–24 hours gives isoxazole (xxv). Cyclization of compound (xxiii) with amidine, urea, thiourea or guanidine in a solvent such as ethanol, dioxane, water or a mixture thereof at a temperature of 25–120° C. for a period of 1–24 hours gives pyrimidine (xxvi) (wherein $X^3$ is a substituent).

Reaction Scheme I

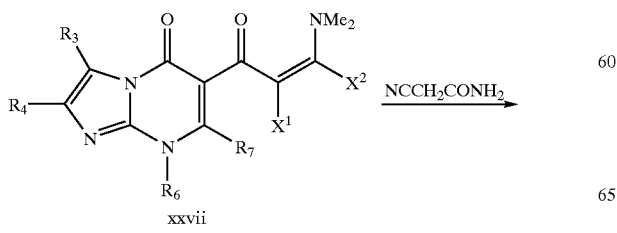

Cyclization of compound (xxvii) (wherein $X^1$ and $X^2$ are substituents) with cyanoacetamide in the presence of a base such as potassium carbonate, potassium tert-butoxide, sodium methoxide in an appropriate solvent such as dioxane, ethanol, DMF at a temperature of 50–150° C. for a period of 1–24 hours gives the pyridone (xxviii). Compound (xxviii) can be converted to the corresponding chloride (xxix) by reaction with $POCl_3$ with or without a solvent such as acetonitrile or toluene at a temperature of 25–120° C. for a period of 1–24 hours. Compound (xxix) can be modified by reaction with a variety of nucleophiles ("Nu⁻") such as mono or dialkylamine, alkoxide, thiol or carbon nucleophile to give compound (xxx).

Palladium catalyzed coupling of compound (xxxi) with arylacetylene in the presence of CuI and a base such as triethylamine in a solvent such as triethylamine, dioxane or DMF at a temperature of 25–120° C. for a period of 1–16 hours gives the alkyne (xxxiv). Selective hydrogenation of the alkyne (xxxiv) catalyzed by palladium/$BaSO_4$ under hydrogen atmosphere in a solvent such as methanol, ethyl acetate or DMF at room temperature for a period of 1–24 hours gives the alkene (xxxv). Further reduction with a catalyst such as palladium on carbon under hydrogen atmosphere in a solvent such as methanol, ethanol or ethyl acetate at room temperature for a period of 1–24 hours gives the corresponding alkane (xxxix).

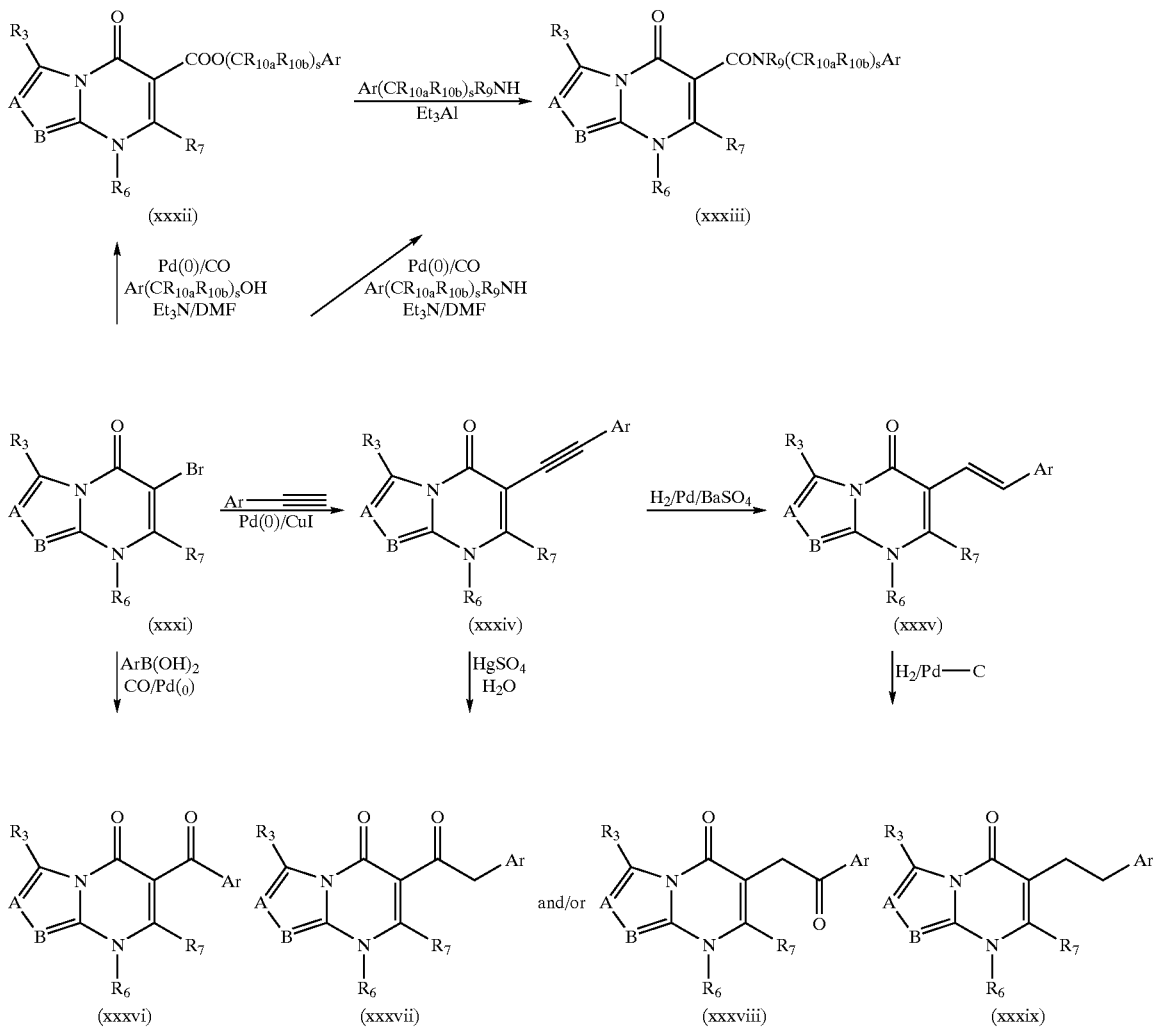

Reaction Scheme J

The bromo compound (xxxi) (see Reaction Scheme H) can be converted to the corresponding carbon analogs by various palladium catalyzed cross coupling reactions. Palladium catalyzed reaction of compound (xxxi) with carbon monoxide in the presence of an alcohol in a solvent such as alcohol or DMF at a temperature of 25–60° C. for a period of 1–24 hours gives the ester (xxxii). Reaction of the ester (xxxii) with a primary or secondary amine and triethylaluminum in a solvent such as dichloromethane or toluene at a temperature of 0–100° C. for a period of 1–16 hours gives the amide (xxxiii).

Palladium catalyzed cross coupling of compound (xxxi) with an arylboronic acid in the presence of a base such as sodium carbonate, cesium carbonate or cesium fluoride in the carbon monoxide atmosphere in a solvent such as benzene, ethanol, water, DME or a mixture thereof at a temperature of 25–100° C. for a period of 1–24 hours gives the ketone (xxxvi).

Reaction of the alkyne xxxiv with $HgSO_4$ in water at a temperature of 25–120° C. for a period of 1–24 hours gives the corresponding ketone (xxxvii) and/or (xxxviii).

Reaction Scheme K

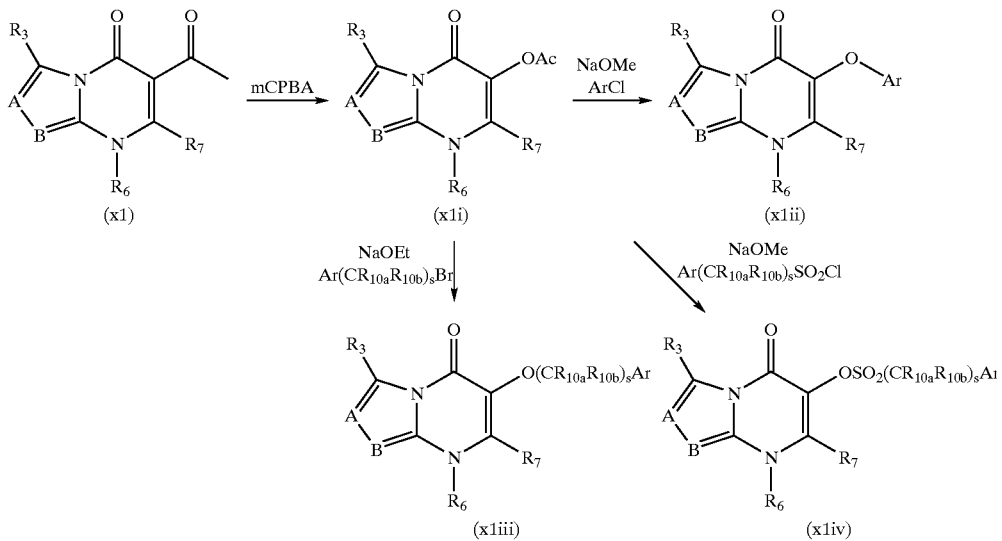

Oxidation of the ketone (xl) with m-chloroperoxybenzoic acid in a solvent such as dichloromethane or chloroform at a temperature of 0–60° C. for a period of 1–72 hours gives the ester (xli). Reaction of compound (xli) with a reactive aryl halide, such as substituted or unsubstituted fluoronitrobenzene, 2- or 4-chloropyridine or 2- or 4-chloropyrimidine, in the presence of a base such as sodium methoxide or potassium t-butoxide in an inert solvent such as THF, DME or DMF at a temperature of 25–120° C. for a period of 1–24 hours gives the aryloxy compound (xlii).

Alkylation of compound (xli) with an aryl alkyl halide in the presence of a base such as sodium ethoxide or potassium hydroxide in as solvent such as THF, DMF or DMSO at a temperature for a period of 1–24 hours gives the corresponding alkoxy compound (xliii). Treatment of the ester (xli) with a base such as sodium methoxide in a solvent such as THF or DMF at room temperature for a period of 0.5 to 2 hours, followed by a sulfonyl chloride at a temperature of 0–60° C. for a period of 1–16 hours gives the sulfonate (xliv).

Reaction Scheme L

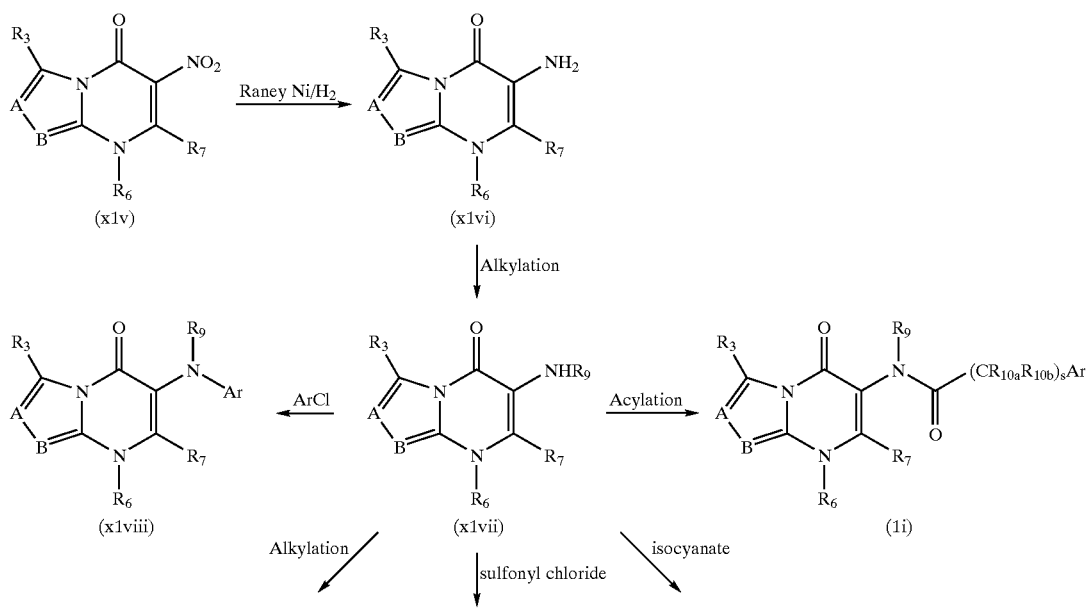

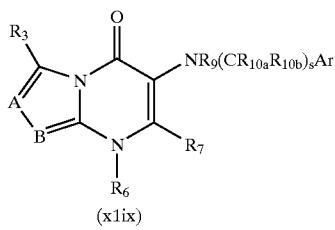
(xlix)

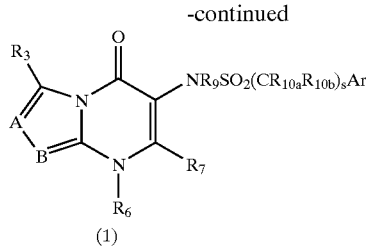
(l)

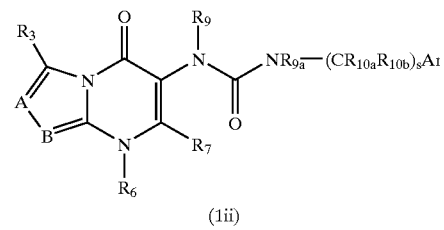
(lii)

The nitro compound (xlv) can be reduced to the corresponding amine (xlvi) by 1) hydrogenation in the presence of a catalyst such as Raney nickel in a solvent such as methanol, ethanol or ethyl acetate at room temperature for a period of 1–24 hours; 2) chemical reduction such as $SnCl_2$ in a solvent such as water at a temperature of 25–100° C. for a period of 1–24 hours. The amine (xlvi) can be alkylated with 1) an alkyl halide in the presence of a base such as potassium carbonate, triethylamine or sodium methoxide in an appropriate solvent such as acetonitrile, ethanol or chloroform at a temperature of 25–100° C. for a period of 1–24 hours; 2) an aldehyde in the presence of a reducing agent such as sodium cyanoborohydride in a solvent such as methanol, dichloromethane or a mixture thereof at a temperature of 25–80° C. for a period of 1–72 hours to give compound (xlvii). Reaction of the primary ($R^9$=H) or secondary amine (xlvii) with a reactive aryl chloride such as chloronitrobenzene, chloropyridine or chloropyrimidine with or without a base such as potassium carbonate, triethylamine or sodium hydride in an appropriate solvent such as THF, DMF or dioxane at a temperature of 25–120° C. for a period of 1–24 hours give the arylamino compound (xlviii). Further alkylation of (xlvii) with an arylalkyl halide with or without a base such as potassium carbonate, triethylamine or sodium hydride in an appropriate solvent such as acetonitrile, THF or DMF at a temperature of 25–100° C. for a period of 1–24 hours give the amino compound (xlix). Reaction of amino compound (xlvii) with sulfonyl chloride in the presence of a base such as triethylamine, pyridine or potassium carbonate in a solvent such as dichloromethane, chloroform or benzene at a temperature of 25–100° C. for a period of 1–24 hours gives the sulfonamide (l). Acylation of the amine (xlvii) with 1) an acid chloride in the presence of a base such as triethylamine, pyridine or potassium carbonate in an appropriate solvent such as dichloromethane, THF or DMF at a temperature of 25–100° C. for a period of 1–16 hours; 2) an carboxylic acid with a coupling reagent such as DCC or EDC in an appropriate solvent such as chloroform or DMF for a period of 1–16 hours gives the corresponding amide (li). Reaction of the amine (xlvii) with an isocyanate in a solvent such as benzene, chloroform or dioxane at a temperature of 25–120° C. for a period of 1–24 hours gives the urea compound (lii).

Reaction Scheme M

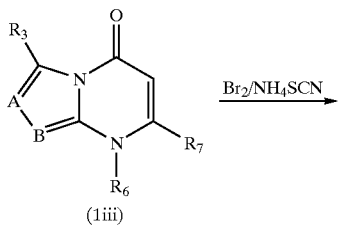
(liii)

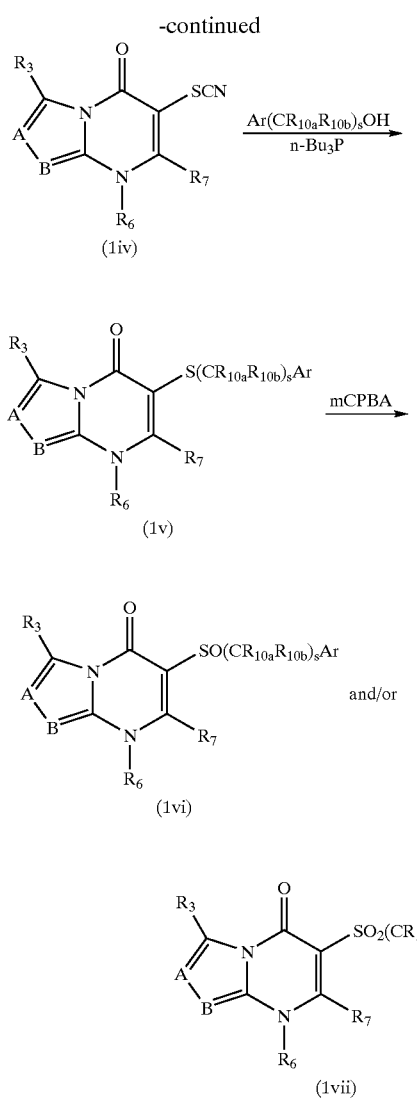

Treatment of compound (liii) with bromine in the presence of ammonium thioisocyanate or potassium isothiocyanate in a solvent such as acetic acid, chloroform or ethanol at a temperature of 0–80° C. for a period of 1–24 hours gives the thioisocyanate (liv). Alkylation of compound (liv) with an alcohol in the presence of tributylphosphine in a solvent such as benzene, chloroform or dioxane at a temperature of 25–120° C. for a period of 1–24 hours gives the sulfide (lv). Oxidation of the sulfide (lv) with an oxidation reagent such as mCPBA or hydrogen peroxide in an appropriate solvent such as dichloromethane, ethanol, water or a mixture thereof at a temperature of 0–60° C. for a period of 1–48 hours gives the corresponding sulfoxide (lvi) and sulfone (lvii).

Reaction Scheme N

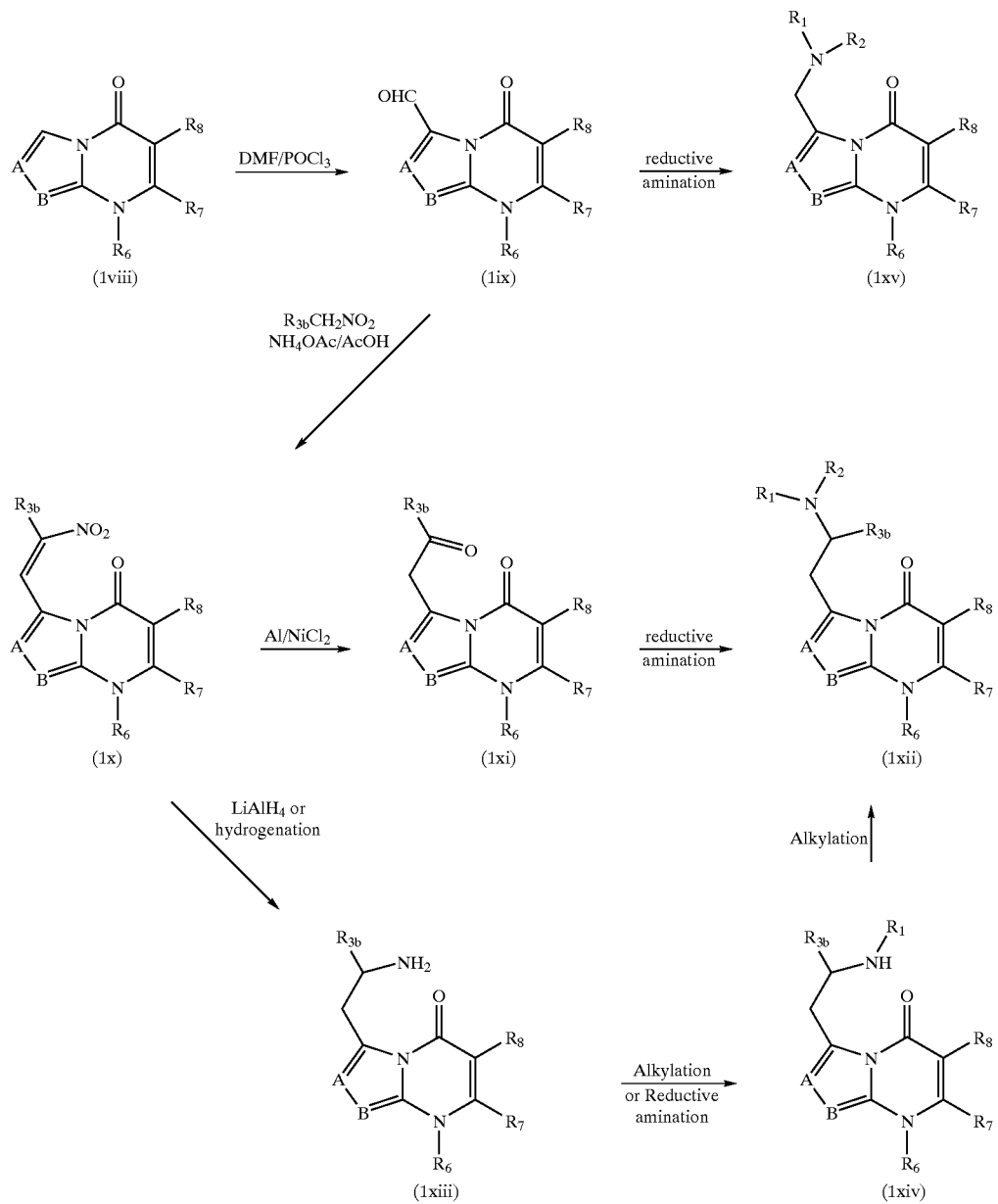

Compound (lviii) can be converted to the corresponding aldehyde (lix) by reaction with $POCl_3$ and DMF at a temperature of 0–120° C. for a period of 1–24 hours. Reductive amination of the aldehyde (lix) with a primary or secondary amine in the presence of a reducing reagent such as sodium cyanoborohydride in an appropriate solvent such as methanol, dichloromethane, THF or a mixture thereof at a temperature of 0–80° C. for a period of 1–24 hours gives the amine (lxv). Condensation of the aldehyde (lix) with nitroalkane in the presence of a base such as ammonium acetate in a solvent such as acetic acid at a temperature of 40–100° C. for a period of 1–24 hours gives the nitroolefin (lx), which can be reduced to the corresponding carbonyl compound (lxi) with a reducing agent such as aluminum in the presence of a catalyst such as nickel chloride in a solvent such as DMF, THF or ethanol at a temperature of 25–100° C. for a period of 1–24 hours. Reductive amination of carbonyl (lxi) with an amine and a reducing agent such as sodium cyanoborohydride in a solvent such as methanol, dichloromethane or mixture thereof at a temperature of 0–80° C. for a period of 1–16 hours gives the amino compound (lxii). Alternatively, the nitroolefin (lx) can be reduced to the corresponding amine (lxiii) by using a reducing agent such as lithium aluminum hydride in an appropriate solvent such as ether or THF at a temperature of 0–80° C. for a period of 1–16 hours, or by hydrogenation with a catalyst such as palladium on carbon under hydrogen atmosphere in a solvent such as methanol or ethyl acetate at room temperature for a period of 1–16 hours. The amine (lxiii) can be converted to the secondary amine (lxiv) or tertiary amine (lxii) by 1) alkylation with an alkyl halide in a solvent such as dichloromethane or ethyl acetate at a temperature of 0–80° C. for a period of 1–16 hours; or 2) reductive amination with an aldehyde and a reducing agent such as sodium cyanoborohydride in a solvent such as methanol, dichloromethane or mixture thereof at a temperature of 0–80° C. for a period of 1–16 hours.

Reaction Scheme O

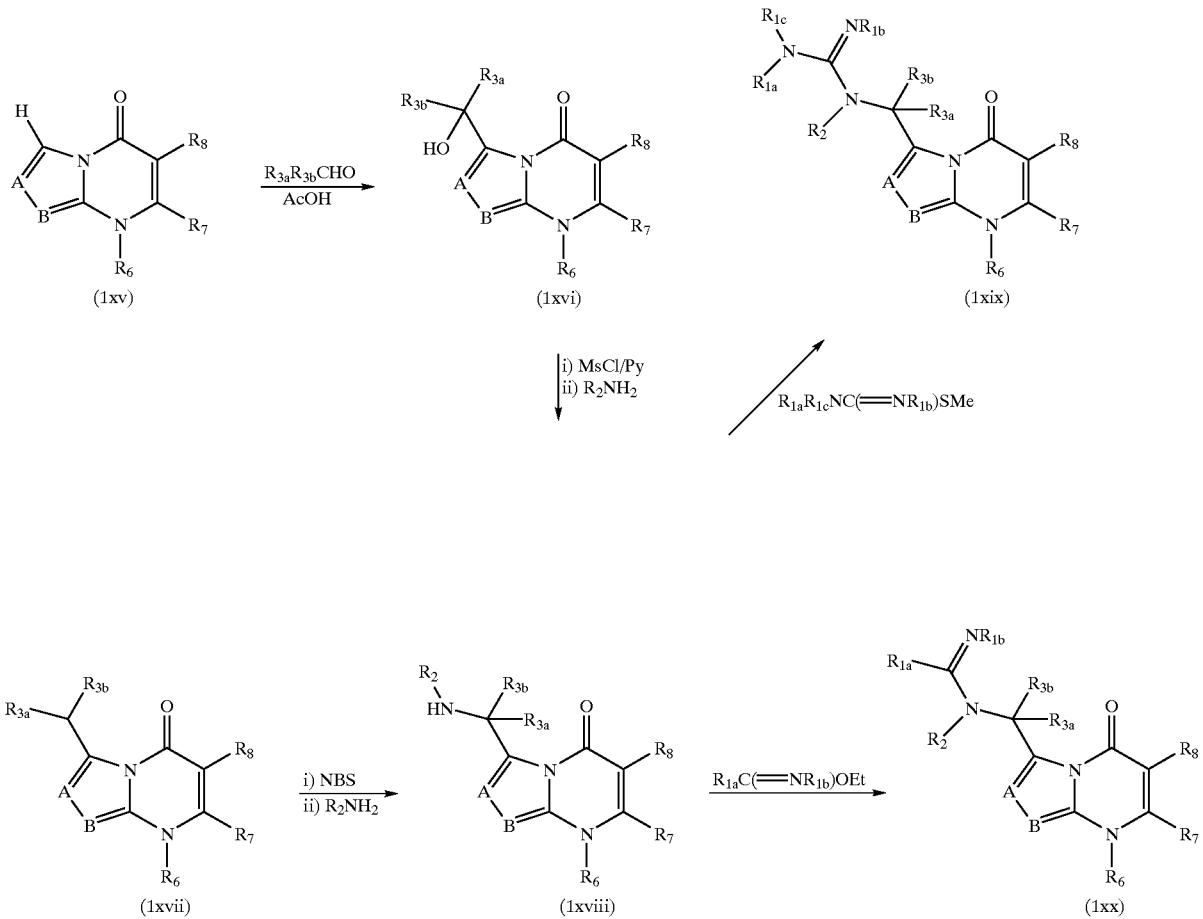

Compound (lxv) can be converted to the corresponding alcohol (lxvi) by reaction with an aldehyde with or without an acid catalyst such as hydrochloric acid, toluenesulfonic acid in an inert solvent such as ethanol, dioxane or acetic acid at a temperature of 25–120° C. for a period of 1–24 hours. Alternatively, the alcohol (lxvi) may be formed first by condensation of an appropriate acid or acid chloride with starting (lxv) to give a ketone followed by reaction with a Grignard or organolithium reagent. The alcohol (lxvi) can be further modified to the corresponding amine (lxviii) by reaction first with methanesulfonyl chloride in the presence of a base such as pyridine, triethylamine in an inert solvent such as dichloromethane, chloroform or pyridine at a temperature of 25–60° C. for a period of 1–24 hours, followed by reaction with ammonium or a primary amine.

Alternatively, bromination of compound (lxvii) with a brominating reagent such as N-succinamide in an inert solvent such as carbon tetrachloride or DMF at a temperature of 25–100° C. for a period of 2–16 hours gives the corresponding bromide (lxviii) which reacts with an amine to give the amino compound (lxviii). The amino compound (lxviii) can be converted to guanidine derivative (lxix) by reaction with a S-methylthiourea in an appropriate solvent such as DMF, THF, ethanol or acetonitrile at a temperature of 25–120° C. for a period of 1–24 hours. The amino compound (lxviii) can also be converted to the corresponding amidine derivative (lxx) by reaction with an imidate in an appropriate solvent such as ethanol, acetonitrile or DMF for a period of 2–24 hours.

Reaction Scheme P

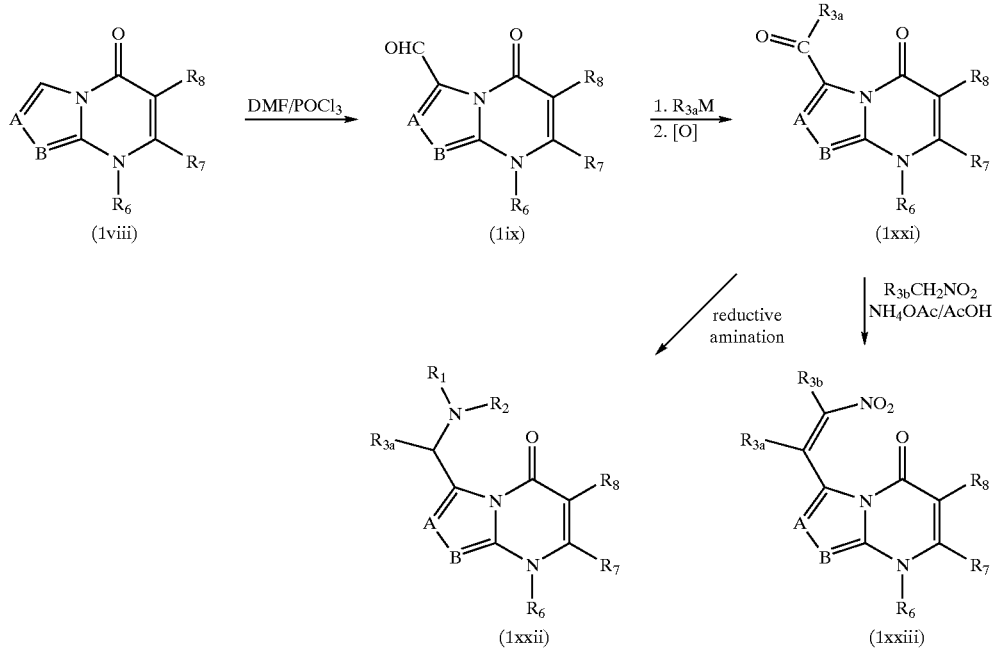

Compound (lviii) can be converted to the corresponding aldehyde (lix) by reaction with POCl$_3$ and DMF at a temperature of 0–120° C. for a period of 1–24 hours. Aldehyde (lix) may then form ketone (lxxi) first through reaction with an appropriate Grignard or organolithium reagent in a solvent such as THF or ethyl ether at a temperature of 78–60° C. followed by an oxidation using Swern conditions or MnO$_2$ or PCC in a solvent such as methylene chloride at a temperature from 0–75° C. Reductive amination of the ketone (lxxi) with a primary or secondary amine in the presence of a reducing reagent such as sodium cyanoborohydride in an appropriate solvent such as methanol, dichloromethane, THF or a mixture thereof at a temperature of 0–80° C. for a period of 1–24 hours gives the amine (lxxii). Condensation of the aldehyde (lxxi) with nitroalkane in the presence of a base such as ammonium acetate in a solvent such as acetic acid at a temperature of 40–100° C. for a period of 1–24 hours gives the nitroolefin (lxxiii).

The compounds of the present invention may generally be utilized as the free base. Alternatively, the compounds of this invention may be used in the form of acid addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of an carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The effectiveness of a compound as a GnRH receptor antagonist may be determined by various assay methods. Suitable GnRH antagonists of this invention are capable of inhibiting the specific binding of GnRH to its receptor and antagonizing activities associated with GnRH. For example, inhibition of GnRH stimulated LH release in immature rats may be measured according to the method of Vilchez-Martinez (*Endocrinology* 96:1130–1134, 1975). Briefly, twenty-five day old male Spraque-Dawley rats are administered an GnRH antagonist in saline or other suitable formulation by oral gavage, subcutaneous injection, or intravenous injection. This is followed by subcutaneous injection of 200 ng GnRH in 0.2 ml saline. Thirty minutes after the last injection, the animals are decapitated and trunk blood collected. After centrifugation, the separated plasma is stored at −200° C. until determination of the LH and FSH by radioimmunoassay. Other techniques for determining the activity of GnRH receptor antagonists are well known in the field, such as the use of cultured pituitary cells for measuring GnRH activity (Vale et al., *Endocrinology* 91:562–572, 1972), and a technique for measuring radioligand binding to rat pituitary membranes (Perrin et al., *Mol. Pharmacol* 23:44–51, 1983).

Activity of GnRH receptor antagonists are typically calculated from the $IC_{50}$ as the concentration of a compound necessary to displace 50% of the radiolabeled ligand from the GnRH receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973). GnRH receptor antagonists of this invention have a $K_i$ of 100 μM or less. In a preferred embodiment of this invention, the GnRH receptor antagonists have a $K_i$ of less than 10 μM, and more preferably less than 1 μM. More preferred compounds include: 1-1, 1-2-5, 12, 13-15, 19, 21, 27, 31, 32, 34, 37, 55, 58, 64, 73, 2B, 2D, 3A, 3B, 3D, 4A, 4B, 4C, 4D, 4G, 4H, 5A and 5B (see Examples below).

Representative GnRH receptor antagonists of this invention include the following compounds:

(a) 3-(N-Benzyl-N-methyl)aminomethyl-2-(tert-butyl)-6-methyl-7-(2-fluorobenzyl)-5-(3-methoxyphenyl)imidazolo[1,2-a]pyrimid-4-one
(b) 3-(N-(2-Pyridylmethyl))aminomethyl-2-(tert-butyl)-6-methyl-7-(2-fluorobenzyl)-5-(3-methoxyphenyl)imidazolo[1,2-a]pyrimid-4-one
(c) 3-(N-(2-Pyridylmethyl)-N-methyl)aminomethyl-2-(tert-butyl)-6-methyl-7-(2-fluorobenzyl)-5-(3-methoxyphenyl)imidazolo[1,2-a]pyrimid-4-one
(d) 3-[N-Methyl-N-(2-pyridylethyl)]aminomethyl-2-(tert-butyl)-6-methyl-7-(2-fluorobenzyl)-5-(3-methoxyphenyl)imidazolo[1,2-a]pyrimid-4-one
(e) 3-[N-(2-Furanmethyl)-N-methyl]aminomethyl-2-(tert-butyl)-6-methyl-7-(2-fluorobenzyl)-5-(3-methoxyphenyl)imidazolo[1,2-a]pyrimid-4-one
(f) 3-[N-Methyl-N-(2-pyridylethyl)]aminomethyl-2-(ethoxycarbonylmethyl)-6-methyl-7-(2-fluorobenzyl)-5-(3-methoxyphenyl)imidazolo[1,2-a]pyrimid-4-one
(g) 1-(N-Benzyl-N-methyl)aminomethyl-2-(tert-butyl)-4-(2-fluorobenzyl)-6-(3-phenylpropylaminocarbonyl)pyrrolo[1,2-a]pyrimid-7-one
(h) 1-[(N-Methyl-N-(2-pyridylethyl)]aminomethyl-2-(tert-butyl)-4-(2-fluorobenzyl)-6-(3-phenylpropylaminocarbonyl)pyrrolo[1,2-a]pyrimid-7-one
(i) 1-[(N-Methyl-N-(2-pyridylethyl)]aminomethyl-2-(tert-butyl)-4-(2-fluorobenzyl)-5-methyl-6-(3-methoxyphenyl)pyrrolo[1,2-a]pyrimid-7-one
(j) 1-(N-Benzyl-N-methyl)aminomethyl-2-(t-butyl)-4-(2-fluorobenzyl)-5-methyl-6-(3-methoxyphenyl)imidazolo[3,4-a]pyrimid-7-one
(k) 1-[N-Methyl-N-(2-pyridylethyl)]aminomethyl-4-(2-fluorobenzyl)-5-methyl-6-(3-methoxyphenyl)imidazolo[3,4-a]pyrimid-7-one
(l) 1-[N-(2-Furanmethyl)-N-methyl]aminomethyl-4-(2-fluorobenzyl)-5-methyl-6-(3-methoxyphenyl)imidazolo[3,4-a]pyrimid-7-one
(m) 3-(N-Benzyl-N-methyl)aminomethyl-6-methyl-7-(2-fluorobenzyl)-5-(3-methoxyphenyl)-1,2,4-triazolo[4,3-a]pyrimid-4-one
(n) 3-[N-Methyl-N-(2-pyridylethyl)]aminomethyl-6-methyl-7-(2-fluorobenzyl)-5-(3-methoxyphenyl)-1,2,4-triazolo[4,3-a]pyrimid-4-one
(o) 3-[N-(2-Furanmethyl)-N-methyl]aminomethyl-6-methyl-7-(2-fluorobenzyl)-5-(3-methoxyphenyl)-1,2,4-triazolo[4,3-a]pyrimid-4-one
(p) 1-(N-Benzyl-N-methyl)aminomethyl-2-(1-methoxycarbonyl-1-methylethyl)-7-(2-fluorobenzyl)-6-methyl-5-(3-methoxyphenyl)imidazolo[1,2-a]pyrimid-4-one
(q) 1-[N-(2-Pyridylethyl)-N-methyl]aminomethyl-2-(1-methoxycarbonyl-1-methylethyl)-7-(2-fluorobenzyl)-6-methyl-5-(3-methoxyphenyl)imidazolo[1,2-a]pyrimid-4-one As mentioned above, the GnRH receptor antagonists of this invention have utility over a wide range of therapeutic applications, and may be used to treat a variety of sex-hormone related conditions in both men and women, as well as mammals in general. For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization).

The compounds of this invention are also useful as an adjunct to treatment of growth hormone deficiency and short stature, and for the treatment of systemic lupus erythematosis.

In addition, the compounds are useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. The compounds may also be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

In another embodiment of the invention, pharmaceutical compositions containing one or more GnRH receptor antagonists are disclosed. For the purposes of administration, the compounds of the present invention may be formulated as pharmaceutical compositions. Pharmaceutical compositions of the present invention comprise a GnRH receptor antagonist of the present invention and a pharmaceutically acceptable carrier and/or diluent. The GnRH receptor antagonist is present in the composition in an amount which is effective to treat a particular disorder—that is, in an amount sufficient to achieve GnRH receptor antagonist activity, and preferably with acceptable toxicity to the patient. Typically, the pharmaceutical compositions of the present invention may include a GnRH receptor antagonist in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GnRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences,* Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration. For oral administration, suitable pharmaceutical compositions of GnRH receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the GnRH receptor antagonist, buffers, antioxidants, bacteriostats, and other additives commonly employed in such solutions.

Rat Anterior Pituitary Cell Culture Assay of GnRH Antagonists

Anterior pituitary glands are collected from 7-week-old female Sprague-Dawley rats and the harvested glands digested with collagenase in a dispersion flask for 1.5 hr at 37° C. After collagenase digestion, the glands are further digested with neuraminidase for 9 min at 37° C. The digested tissue is then washed with 0.1% BSA/McCoy's 5A medium, and the washed cells suspended in 3% FBS/0.1 BSA/McCoy's 5A medium and plated into 96-well tissue culture plates at a cell density of 40,000 cells per well in 200 $\mu$l medium. The cells are then incubated at 37° C. for 3 days. One pituitary gland normally yields one 96-well plate of cells, which can be used for assaying three compounds. For assay of an GnRH antagonist, the incubated cells are first washed with 0.1% BSA/McCoy's 5A medium once, followed by addition of the test sample plus 1 nM GnRH in 200 $\mu$l 0.1% BSA/McCoy's 5A medium in triplicate wells. Each sample is assayed at 5-dose levels to generate a dose-response curve for determination of its potency on the inhibition of GnRH stimulated LH and/or FSH release. After 4-hr incubation at 37° C., the medium is harvested and the level of LH and/or FSH secreted into the medium determined by RIA.

RIA of LH and FSH

For determination of the LH levels, each sample medium is assayed in duplicates and all dilutions are done with RIA buffer (0.01M sodium phosphate buffer/0.15M NaCl/1% BSA/0.01% NaN3, pH 7.5) and the assay kit is obtained from the Nation Hormone and Pituitary Program supported by NIDDK. To a 12×75 mm polyethylene test tube is added 100 $\mu$l of sample medium diluted 1:5 or rLH standard in RIA buffer and 100 $\mu$l of [125I]-labeled rLH (~30,000 cpm) plus 100 $\mu$l of rabbit anti-rLH antibody diluted 1:187,500 and 100 $\mu$l RIA buffer. The mixture is incubated at room temperature over-night. In the next day, 100 $\mu$l of goat anti-rabbit IgG diluted 1:20 and 100 $\mu$l of normal rabbit serum diluted 1:1000 are added and the mixture incubated for another 3 hr at room temperature. The incubated tubes are then centrifuged at 3,000 rpm for 30 min and the supernatant removed by suction. The remaining pellet in the tubes is counted in a gamma-counter. RIA of FSH is done in a similar fashion as the assay for LH with substitution of the LH antibody by the FSH antibody diluted 1:30,000 and the labeled rLH by the labeled rFSH.

Radio-iodination of GnRH Peptide

The GnRH analog is labeled by the chloramine-T method. To 10 $\mu$g of peptide in 20 $\mu$l of 0.5M sodium phosphate buffer, pH 7.6, is added 1 mCi of Na125I, followed by 22.5 $\mu$g chloramine-T and the mixture vortexed for 20 sec. The reaction is stopped by the addition of 60 $\mu$g sodium metabisulfite and the free iodine is removed by passing the iodinated mixture through a C-8 Sep-Pak cartridge (Millipore Corp., Milford, Mass.). The peptide is eluted with a small volume of 80% acetonitrile/water. The recovered labeled peptide is further purified by reverse phase HPLC on a Vydac C-18 analytical column (The Separations Group, Hesperia, Calif.) on a Beckman 334 gradient HPLC system using a gradient of acetonitrile in 0.1% TFA. The purified radioactive peptide is stored in 0.1% BSA/20% acetonitrile/0.1% TFA at −800 C. and can be used for up to 4 weeks.

GnRH Receptor Membrane Binding Assay

Cells stably, or transiently, transfected with GnRH receptor expression vectors are harvested, resuspended in 5% sucrose and homogenized using a polytron homogenizer (2×15 sec). Nuclei are removed by centrifugation (3000×g for 5 min.), and the supernatant centrifuged (20,000×g for 30 min, 4° C.) to collect the membrane fraction. The final membrane preparation is resuspended in binding buffer (10 mM Hepes (pH 7.5), 150 mM NaCl, and 0.1% BSA) and stored at −70° C. Binding reactions are performed in a Millipore MultiScreen 96-well filtration plate assembly with polyethylenimine coated GF/C membranes. The reaction is initiated by adding membranes (40 ug protein in 130 ul binding buffer) to 50 ul of [$^{125}$I]-labeled GnRH peptide (~100,000 cpm), and 20 ul of competitor at varying concentrations. The reaction is terminated after 90 minutes by application of vacuum and washing (2×) with phosphate buffered saline. Bound radioactivity is measured using 96-well scintillation counting (Packard Topcount) or by removing the filters from the plate and direct gamma counting. $K_i$ values are calculated from competition binding data using non-linear least squares regression using the Prism software package (GraphPad Software).

The following examples are provided for purposes of illustration, not limitation. In summary, the GnRH receptor antagonists of this invention may be assayed by the methods disclosed above, while Examples 1–4 disclose the synthesis of representative compounds of this invention.

EXAMPLE 1

Synthesis of 2-(tert-butyl)-3-[N-methyl-N-(2-pyridylethyl)aminomethyl]-5-(3-methoxyphenyl)-6-methyl-7-(2-fluorobenzyl)immidazolo[1,2-a]pyrimid-4-one

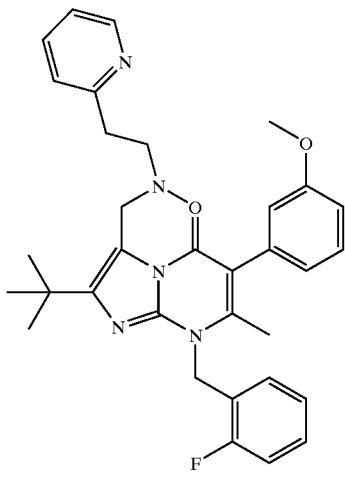

Step 1A 5-Bromo-6-methyl-2-(tert-butyl)-7H-imidazolo[1,2-a]pyrimid-4-one

Under nitrogen atmosphere, to a solution of 2-amino-5-bromo-4-hydroxy-6-methylpyrimidine (4.08 g, 20 mmol.) in dry DMF (80 ml), sodium hydride (800 mg, 20 mmol., 60% in mineral oil) was carefully added. The mixture was stirred at room temperature for 0.5 hour, followed by addition of bromomethyl tert-butyl ketone (20 mmol.). The mixture was then stirred at room temperature overnight. The resultant mixture was concentrated in vacuo, and the residue was dissolved in acetone (50 ml) and diluted with water (100 ml). Slowly concentration under reduced pressure resulted in a precipitation. The solid was collected by filtration, washing with water, ether, and dried to yield the desired product as a white powder (4.16 g, 80% yield); MS: 284/286 (M+H)$^+$.

Step 1B 5-(3-methoxyphenyl)-6-methyl-2-(tert-butyl)-7H-imidazolo[1,2-a]pyrimid-4-one To a pressure vessel, potassium carbonate (1.38 g, 10 mmol.), 3-methoxyphenylboronic acid (1.06 g, 7.0 mmol.), 5-bromo-6-methyl-2-(tert-butyl)-7H-imidazolo[1,2-a]pyrimid-4-one (1.42 g, 5 mmol), toluene (20 ml), water (5 ml) were added. The mixture was bubbled by nitrogen gas for 10 minutes to remove the air. Then Pd(PPh$_3$)$_4$ (500 mg) was added and the vessel was sealed immediately and heated at 110° C. for 6 hours. After cooled to room temperature, the mixture was extracted with ethyl acetate (100 ml). The ethyl acetate layer was washed with water, dried and concentrated to give a yellow solid. It was stirred with a mixture of ether/ethyl acetate (50 ml/5 ml) and solid was collected by filtration to give the crude product (0.74 g); MS: 312 (M+H)$^+$.

Step 1C 5-(3-methoxyphenyl)-6-methyl-2-(tert-butyl)-7-(2-fluorophenylmethyl)-imidazolo[1,2-a]pyrimid-4-one To a solution of 5-(3-methoxyphenyl)-6-methyl-2-(tert-butyl)-7H-imidazolo[1,2-a]pyrimid-4-one (0.74 g, 2.4 mmol.) in DME (5 ml), tetrabutylammonium fluoride (4 ml, 1.0 M in THF) was added and followed by addition of 2-fluorobenzyl bromide (0.45 ml, 1.5 eq.). The mixture was stirred at room temperature overnight and then concentrated and purified by silica gel chromatography (hexane/ethyl acetate) to give the desired product (0.55 g) as a white powder; MS: 420(M+H)$^+$; NMR (CDCl$_3$, δ): 7.38–6.77 (9H, 4m), 5.69 (2H, s), 3.80(3H, s), 2.20 (3H, s), 1.32 (9H, s).

Step 1D 3-{N-methyl-N-[2-(2-pyridyl)ethyl]aminomethyl}-5-(3-methoxyphenyl)-6-methyl-2-(tert-butyl)-7-(2-fluorophenylmethyl)-imidazolo[1,2-a]pyrimid-4-one To a solution of N-[2-(2-pyridylethyl)]-N-methylamine (136 mg, 1.0 mmol.) and aqueous formaldehyde (0.1 ml) in acetic acid (2 ml), 5-(3-methoxyphenyl)-6-methyl-2-(tert-butyl)-7-(2-fluorophenylmethyl)-imidazolo[1,2-a]pyrimid-4-one (210 mg, 0.5 mmol) was added. The solution was stirred at room temperature for 1 hours and directly purified by prep HPLC to give the pure product (240 mg) as a trifluoroacetic acid salt; MS: 568(M+H)$^+$, 432. NMR (DMSO-d$_6$, δ): 9.16 (1H, brs), 8.21 (1H, d), 7.80 (1H, t), 7.39–6.86 (10H, m), 5.65 (2H, s), 4.85 (2H, s), 3.78 (3H, s), 3.66 (2H, brs), 3.28 (2H, t), 2.97 (3H, s), 2.27 (3H, s), 1.35 (9H, s).

Following the procedure similar to that described above, the following compounds were prepared:

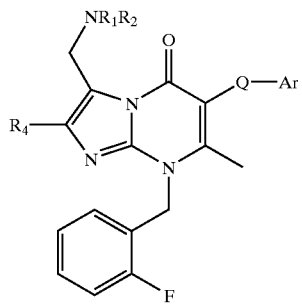

| Example | R₁NR₂ | R₄ | —Q—Ar | MS (M + H)⁺ |
|---|---|---|---|---|
| 1-1 | 2-PyCH₂CH₂NMe | t-Bu | 3-OMe—Ph | 568 |
| 1-2 | BnNMe | t-Bu | 3-OMe—Ph | 553 |
| 1-3 | FurylCH₂NMe | t-Bu | 3-OMe—Ph | 543 |
| 1-4 | Me₂NCH₂CH₂NMe | t-Bu | 3-OMe—Ph | 534 |
| 1-5 | MeOCH₂CH₂NMe | t-Bu | 3-OMe—Ph | 521 |
| 1-6 | —N(piperazine)N— | t-Bu | 3-OMe—Ph | 532 |
| 1-7 | 2-PyCH₂CH₂NMe | i-Bu | 3-OMe—Ph | 568 |
| 1-8 | BnNMe | i-Bu | 3-OMe—Ph | 553 |
| 1-9 | 2-PyCH₂CH₂NMe | Me | 3-OMe—Ph | 526 |
| 1-10 | BnNMe | Me | 3-OMe—Ph | 511 |
| 1-11 | benzimidazolylmethyl-NMe | t-Bu | 3-OMe—Ph | 593 |
| 1-12 | 2-PyCH₂NMe | t-Bu | 3-OMe—Ph | 554 |
| 1-13 | 2-PyCH₂CH₂NMe | 2-OH-t-Bu | 3-OMe—Ph | |
| 1-14 | PhCH₂NMe | t-Bu | Ph | 523 |
| 1-15 | 2-PyCH₂CH₂NMe | t-Bu | 2-Py | 538 |
| 1-16 | PhCH₂NMe | t-Bu | Ph | 524 |
| 1-17 | BuNMe | t-Bu | Ph | |
| 1-18 | 4-benzylpiperidinyl | t-Bu | Ph | |
| 1-19 | 2-FurylCH₂NMe | t-Bu | Ph | 513 |
| 1-20 | 4-methylpiperazinyl | t-Bu | Ph | 502 |
| 1-21 | PhCH₂NMe | methyl-butyrolactone | 3-OMe—Ph | 595 |
| 1-22 | PhCH₂NCH₂CH₂CN | methyl-butyrolactone | 3-OMe—Ph | 634 |

-continued

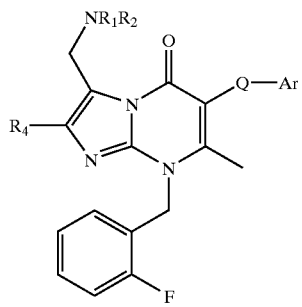

| Example | R₁NR₂ | R₄ | —Q—Ar | MS (M + H)⁺ |
|---|---|---|---|---|
| 1-23 | (1,3-benzodioxol-5-ylmethyl)piperazinyl | | 3-OMe—Ph (γ-butyrolactone) | 694 |
| 1-24 | 4-(4-chlorophenyl)-4-hydroxypiperidinyl | | 3-OMe—Ph (γ-butyrolactone) | 685 |
| 1-25 | 4-hydroxy-4-(3-trifluoromethylphenyl)piperidinyl | | 3-OMe—Ph (γ-butyrolactone) | 719 |
| 1-26 | 4-(4-trifluoromethyl-2-nitrophenyl)piperazinyl | | 3-OMe—Ph (γ-butyrolactone) | 749 |
| 1-27 | 2-FurylCH₂NMe | | 3-OMe—Ph (γ-butyrolactone) | 585 |
| 1-28 | Me₂NCH₂CH₂NMe | | 3-OMe—Ph (γ-butyrolactone) | 576 |
| 1-29 | 2-PyCH₂NH | | 3-OMe—Ph (γ-butyrolactone) | 582 |
| 1-30 | PhCH₂NMe | t-Bu | 3-Py | 524 |
| 1-31 | PhCH₂NMe | t-Bu | 3-AcPh | 565 |
| 1-32 | 2-PyCH₂CH₂NMe | t-Bu | 3-AcPh | 580 |
| 1-33 | 2-FurylCH₂NMe | t-Bu | 3-AcPh | 555 |
| 1-34 | 2-PyCH₂NH | t-Bu | 3-OMe—Ph | 552 |
| 1-35 | Me₂NCH₂CH₂NMe | t-Bu | 3-OMe—Ph | 546 |

-continued
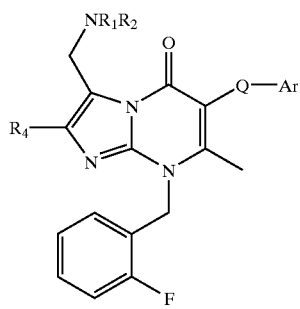
| Example | R₁NR₂ | R₄ | —Q—Ar | MS (M + H)⁺ |
|---|---|---|---|---|
| 1-36 | (R)-N(Me)-CH(Me)-Ph | t-Bu | 3-OMe—Ph | 567 |
| 1-37 | (S)-N(Me)-CH(Me)-Ph | t-Bu | 3-OMe—Ph | 567 |
| 1-38 | N(Me)-CH(Me)-(1-naphthyl) | t-Bu | 3-OMe—Ph | 617 |
| 1-39 | NH-CH(Me)-Ph | t-Bu | 3-OMe—Ph | 553 |
| 1-40 | NH-C(Me)₂-Ph | t-Bu | 3-OMe—Ph | 567 |

-continued
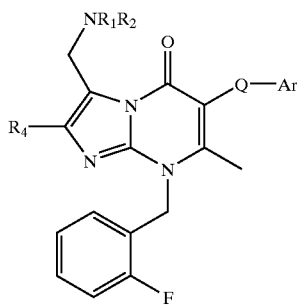
| Example | R₁NR₂ | R₄ | —Q—Ar | MS (M + H)⁺ |
|---|---|---|---|---|
| 1-41 | (S)-N-methyl-1-(naphthalen-1-yl)ethylamine | t-Bu | 3-OMe—Ph | 432, 603 |
| 1-42 | N-methylbenzylamine | t-Bu | phenylethynyl | 456, 577 |
| 1-43 | N-methylbenzylamine | t-Bu | 2-F—Bn | 434, 555 |
| 1-44 | N-methylbenzylamine | t-Bu | 2-F—Ph | 541 |
| 1-45 | N-butylbenzylamine | t-Bu | 2-F—Ph | 583 |
| 1-46 | thiomorpholine | t-Bu | 2-F—Ph | 523 |

-continued
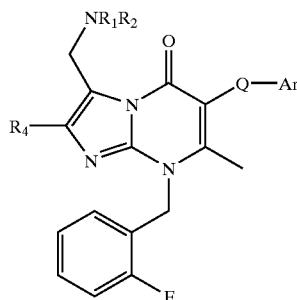
| Example | R₁NR₂ | R₄ | —Q—Ar | MS (M + H)⁺ |
|---|---|---|---|---|
| 1-47 | 3,3-dimethylpiperidin-1-yl | t-Bu | 2-F—Ph | 533 |
| 1-48 | —N(CH₃)CH₂CH₂CH₂-morpholine | t-Bu | 2-F—Ph | 564 |
| 1-49 | —N(CH₃)CH₂-(2-furyl) | t-Bu | 2-F—Ph | 531 |
| 1-50 | —N(CH₃)CH₂CH₂CH₂N(Et)₂ | t-Bu | 2-F—Ph | 564 |
| 1-51 | —N(CH₃)CH₂-(1,3-dioxolan-2-yl) | t-Bu | 2-F—Ph | 537 |
| 1-52 | —N(CH₃)CH₂CH₂OCH₃ | t-Bu | 2-F—Ph | 509 |
| 1-53 | —N(CH₃)CH₂CH₂CH₂N(CH₃)₂ | t-Bu | 2-F—Ph | 536 |

-continued
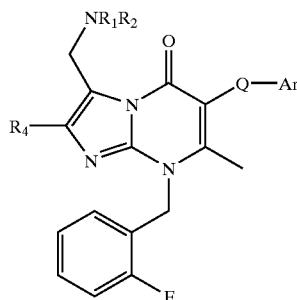
| Example | R₁NR₂ | R₄ | —Q—Ar | MS (M + H)⁺ |
|---|---|---|---|---|
| 1-54 | 2-PyCH₂CH₂NMe | t-Bu | 3-(1-hydroxyethyl)phenyl | 582 |
| 1-55 | 2-PyCH₂CH₂NMe | t-Bu | 2-F—Ph | 556 |
| 1-56 | 3-hydroxy-3-phenyl-N-methylpropylamino | t-Bu | 2-F—Ph | 420 |
| 1-57 | 2-PyCH₂CH₂NMe | t-Bu | 1,3-benzodioxol-5-yl | 446 |
| 1-58 | 2-PyCH₂NMe | t-Bu | 1,3-benzodioxol-5-yl | 446 |
| 1-59 | N-ethyl-1-benzylpyrrolidin-3-ylamino | t-Bu | 1,3-benzodioxol-5-yl | 446 |
| 1-60 | 3,3-dimethylpiperidin-1-yl | t-Bu | 1,3-benzodioxol-5-yl | 559 |

-continued
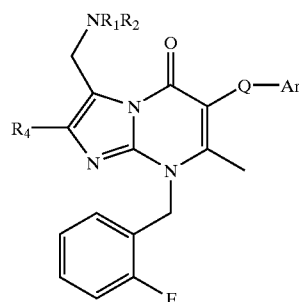
| Example | R₁NR₂ | R₄ | —Q—Ar | MS (M + H)⁺ |
|---|---|---|---|---|
| 1-61 | N-benzyl-N-butyl | t-Bu | benzodioxole | 446 |
| 1-62 | thiomorpholine | t-Bu | benzodioxole | 446 |
| 1-63 | (dimethylamino)propyl-N-methyl | t-Bu | benzodioxole | 562 |
| 1-64 | methoxyethyl-N-methyl | t-Bu | benzodioxole | 446 |
| 1-65 | (1,3-dioxan-2-yl)methyl-N-methyl | t-Bu | benzodioxole | 446 |
| 1-66 | (diethylamino)propyl-N-methyl | t-Bu | benzodioxole | 590 |

-continued
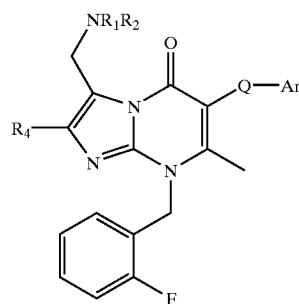
| Example | R₁NR₂ | R₄ | —Q—Ar | MS (M + H)⁺ |
|---|---|---|---|---|
| 1-67 | pyrrolidin-1-yl | t-Bu | benzo[1,3]dioxol-5-yl | 446 |
| 1-68 | N-butyl-N-methylamino | t-Bu | benzo[1,3]dioxol-5-yl | 446 |
| 1-69 | 4-(3-chlorophenyl)piperidin-1-yl | t-Bu | benzo[1,3]dioxol-5-yl | 446 |
| 1-70 | 4-(benzyloxycarbonyl)piperazin-1-yl | t-Bu | benzo[1,3]dioxol-5-yl | 446 |
| 1-71 | 4-phenylpiperazin-1-yl | t-Bu | benzo[1,3]dioxol-5-yl | 446 |
| 1-72 | (4-methylpiperazin-1-yl)(methyl)amino | t-Bu | benzo[1,3]dioxol-5-yl | 446 |

-continued

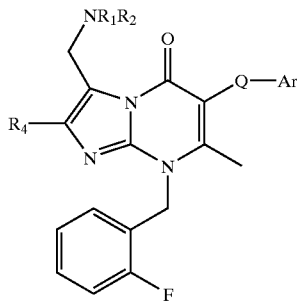

| Example | R₁NR₂ | R₄ | —Q—Ar | MS (M + H)⁺ |
|---|---|---|---|---|
| 1-73 | Et₂NCH₂CH₂NMe | t-Bu | (1,3-benzodioxol-5-yl) | 576 |

EXAMPLE 2.1

Synthesis of 1-(N-Benzyl-N-Methylaminomethyl)-2-(tert-butyl)-4-(2-fluorobenzyl)-6-ethoxycarbonylpyrrolo[1,2-a]pyrimid-7-one (Intermediate)

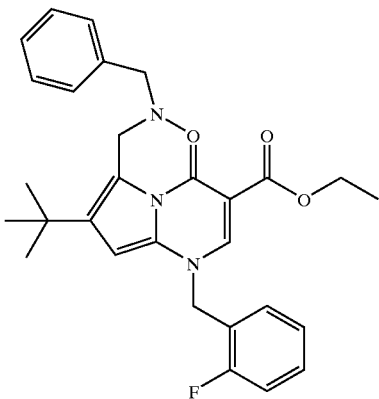

Step 2A 5-Ethoxycarbonyl-2-methyl-3-(2-oxo-3,3-dimethyl-butyl)pyrimid-4-one To a suspension of 5-ethoxycarbonyl-2-methylpyrimid-4-one (2.7 g, 14.75 mmol.) in DME (20 ml), tetrabutylammonium fluoride (22 ml, 22.0 mmol.) was added. The solution was stirred at room temperature until solids dissolved, then 1-bromopinacolone (2.2 ml, 1.1 eq., 16.22 mmol) was added. The solution was stirred overnight and concentrated to a brown oil. The crude mixture was purified by silica gel column chromatography (hexane/ethyl acetate, 100/0 to 0/100). A less polar O-alkylated by-product was eluted first (1.8 g) and then the desired N-alkylated product (1.1 g); MS (281, M+H)⁺. NMR (CDCl₃, δ): 8.57 (1H, s), 5.06(1H, s), 4.35(2H, q), 2.42 (3H, s), 1.34 (3H, t), 1.30 (9H,s).

Step 2B 6-Ethoxycarbonyl-2-(tert-butyl)-4H-pyrrolo[1,2-a]pyrimid-7-one

5-Ethoxycarbonyl-2-methyl-3-(2-oxo-3,3-dimethyl-butyl)pyrimid-4-one (1.1 g, 3.9 mmol.) was added into sodium ethoxide solution, made in situ from sodium (200 mg) and dry ethanol (50 ml). After stirred for 2 hours, the mixture was acidified slowly with 6N HCl resulting a precipitation. The precipitates were collected by filtration and washed with water (20 ml×2), ether (20 ml×3), dried to give the desired product (0.8 g); MS (263, M+H)⁺.

Step 2C 6-Ethoxycarbonyl-2-(tert-butyl)-4-(2-fluorobenzyl)pyrrolo[1,2-a]pyrimid-7-one To 6-ethoxycarbonyl-2-(tert-butyl)-4H-pyrrolo[1,2-a]pyrimid-7-one (0.5 g, 1.9 mmol.) in DME (5 ml), tetrabutylammonium fluoride (4 ml, 4.0M in THF) was added, and a white foamy material formed. 2-Fluorobenzyl bromide (0.38 ml, 3 mmol.) was added and the mixture was stirred at room temperature for 2 days. Concentration of the reaction mixture in vacuo produced an oil, which was dissolved in acetone (20 ml) and diluted with water until the solution turned a slight cloudy. Partially concentration to remove acetone by nitrogen flow resulting precipitation. The precipitates were collected by filtration and washed with water (20 ml×2), ether (20 ml×3) and dried. The desired product (0.57 g) was obtained with excellent purity; MS: 371 (M+H)⁺, 325; NMR (CDCl₃, δ): 8.29 (1H, s), 7.43–7.14(5H, 2m), 5.99 (1H, s) 5.18 (2H,s ), 4.35 (2H, q), 1.37(3H, s), 1.26 (9H, s).

Step 2D 6-Ethoxycarbonyl-3-(N-benzyl-N-methylaminomethyl)-2-(tert-butyl)-7-(2-fluorobenzyl)pyrrolo[1,2-a]pyrimid-7-one Formaldehyde in water (1 drop) and N-benzyl-N-methylamine (2 drops) were added to acetic acid (1 ml) and stirred for 5 minutes. The 6-ethoxycarbonyl-2-(tert-butyl)-7-(2-fluorobenzyl)pyrrolo[1,2-a]pyrimid-7-one (20 mg, 0.05 mmol) was added. The solution was stirred at room temperature for 1 hour and concentrated to an oil. It was then neutralized by potassium carbonated (saturated) and the crude product was purified by prep TLC plate using CHCl₃/MEOH/NH₄OH (400/50/2) to give the desired compound (11.1 mg); MS: 504(M+H)⁺, 383. NMR (CDCl₃, δ): 8.18 (1H, s), 7.41–7.13 (9H, m), 5.93 (1H, s), 5.10(2H, s), 4.47 (2H, s), 4.36 (2H, q), 3.62 (2H, s), 2.08 (3H, s), 1.34 (9H, s). 1.34 (3H, t).

Following a procedure similar to that described above, the following intermediates were prepared:

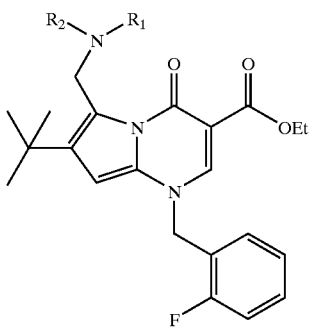

| Example | R₁NR₂ | MS (M + H⁺) |
|---------|-------|-------------|
| 2A | BnNMe | 504 |
| 2B | 2-PyCH₂CH₂NMe | 519 |

EXAMPLE 2.2

Synthesis of 1-(N-Benzyl-N-methylaminomethyl)-2-(tert-butyl)-4-(2-fluorobenzyl)-6-[(3-phenylpropylamino)carbonyl]pyrrolo[1,2-a]pyrimid-7-one

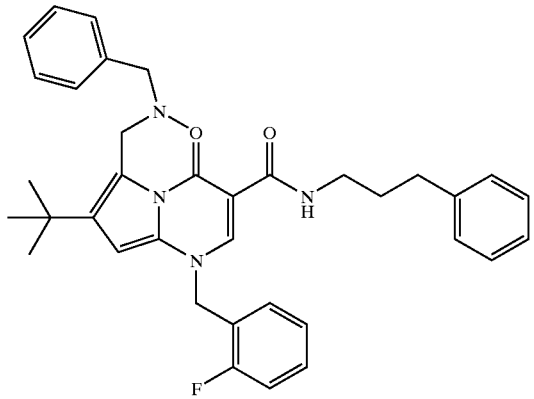

Step 2E 6-(3-Phenylpropylaminocarbonyl)-2-(tert-butyl)-7-(2-fluorobenzl)pyrrolo[1,2-a]pyrimid-7-one To a solution of 3-phenyl-1-propylamine (0.27 g, 2.0 mmol.) in DME (3 ml) under nitrogen atmosphere, triethylaluminum (0.5 ml, 1.9 M in toluene) was added. The solution was stirred at room temperature for 0.5 hour, followed by addition of 6-ethoxycarbonyl-2-(tert-butyl)-7-(2-fluorobenzyl)pyrrolo[1,2-a]pyrimid-7-one (135 mg, 0.5 mmole). The solution was then heated at 50° C. overnight and poured into a 6N HCl solution (5 ml). The crude product was extracted out by ethyl acetate (50 ml). The organic layer was filtered through a silica pad (2 g) and concentrated to give the desired product (100 mg) which was pure based on TLC (hexane/ethyl acetate=1/1) and used for the next step; MS: 460 (M+H)⁺.

Step 2F 6-(3-Phenylpropylaminocarbonyl)-2-(tert-butyl)-3-(N-benzyl-N-methylaminomethyl)-7-(2-fluorobenzyl)pyrrolo[1,2-a]pyrimid-7-one To a solution of formaldehyde (37% aqueous, 1 drop) and N-benzyl-N-methylamine (1 drop) in acetic acid (1 ml) was added 6-(3-phenylpropylaminocarbonyl)-2-(tert-butyl)-4-(2-fluorobenzyl)pyrrolo[1,2-a]pyrimid-7-one (14 mg, 0.03 mmol). The mixture was stirred at room temperature for 1 hour and concentrated in vacuo. The crude product was purified on prep-TLC plates using CHCl₃/MEOH/NH₄OH (400/50/2) to give the desired product (13 mg); MS: 593 (M+H)⁺, 472; NMR (CDCl₃, δ) 9.29 (1H, t), 8.43 (1H, s), 7.34–7.11 (14H, m), 5.95 (1H, s), 5.13 (2H, s), 4.42 (2H, s), 3.60 (2H, s), 3.46 (2H, m), 2.73 (2H, t), 2.23 (3H, s), 2.01 (2H, m), 1.38 (9H, s).

Following a procedure similar to that described above, the following compounds were prepared:

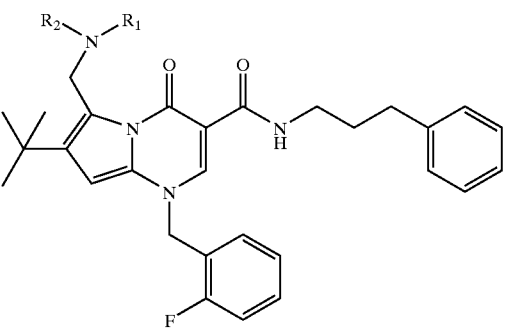

| Example | R₁NR₂ | MS (M + H)⁺ |
|---------|-------|-------------|
| 2C | BnNMe | 593 |
| 2D | 2-PyCH₂CH₂NMe | 608 |

EXAMPLE 3

Synthesis of 2-(tert-butyl)-3-[N-(2-fluorophenyl)ethyl]aminomethyl-5-(3-methoxyphenyl)-6-methyl-7-(2-fluorobenzyl)immidazolo[1,2-a]pyrimid-4-one

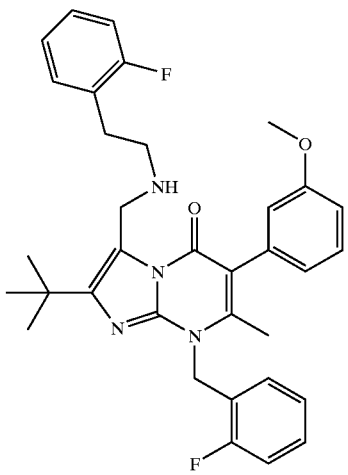

Step 3A. 2-(tert-Butyl)-3-formyl-5-(3-methoxyphenyl)-6-methyl-7-(2-fluorobenzyl)imidazolo[1,2-a]pyrimid-4-one To a solution of 2-(tert-butyl)-5-(3-methoxyphenyl)-6-methyl-7-(2-fluorobenzyl)imidazolo[1,2-a]pyrimid-4-one (850 mg, 2.02 mmol.) in dry DMF (2 ml), POCl$_3$(1 ml) was added. The mixture was heated at 50° C. for 10 minutes and ethyl acetate (200 ml ) was added, followed by addition of saturated sodium bicarbonate slowly until it is neutral. The organic layer was dried and concentrated to give the crude product (910 mg) as a yellow solid; MS: 448 (M+H)$^+$.

Step 3B 2-(tert-Butyl)-3-[N-(2-fluorophenyl)ethyl]aminomethyl-5-(3-methoxyphenyl)-6-methyl-7-(2-fluorobenzyl)imidazolo[1,2-a]pyrimid-4-one To a solution of 2-(tert-butyl)-3-formyl-5-(3-methoxyphenyl)-6-methyl-7-(2-fluorobenzyl)imidazolo[1,2-a]pyrimid-4-one (20 mg, 0.045 mmol.) in 1.2-dichloroethane (1 ml), 2-(2-fluorophenyl)-ethylamine (12.5 mg, 2.0 eq.) was added, followed by addition of sodium triacetoxyborohydride (48 mg, 5 eq.). The mixture was stirred at room temperature overnight. The product (12.9 mg) was isolated by a prep-TLC plate (0.5 mm thickness, 20×20 cm size) using CHCl$_3$/MeOH/NH$_4$OH (400/50/2) as elution solvents; MS: 571(M+H)$^+$, 432. NMR (CDCl$_3$, δ): 7.36–6.72 (12H, m), 5.63(2H,s), 4.28(2H,s), 3.81(3H,s), 3.05–2.87 (4H,m), 2.16(3H,s), 1.40(9H,s).

Following a procedure similar to that described above, the following compounds were prepared:

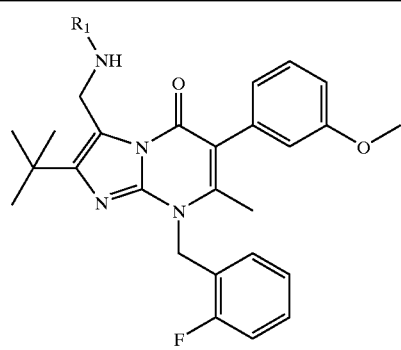

| Example | R$_1$ | MS (M + H)$^+$ |
|---|---|---|
| 3A | (2-FPh)CH$_2$CH$_2$ | 571 |
| 3B | (2-Py)CH$_2$CH$_2$ | 554 |
| 3C | PhCH$_2$CH$_2$CH$_2$CH$_2$ | 581 |
| 3D | 2-PyCH$_2$ | 540 |
| 3E | EtOCH$_2$CH$_2$CH$_2$ | 535 |

EXAMPLE 4.1

Synthesis of 2-(1-methoxycarbonyl-1-methylethyl)-3-{N-[(2-pyridyl)ethyl]aminomethyl}-5-bromo-6-methyl-7-(2-flurorbenzyl)immidazolo[1,2-a]pyrimid-4-one (Intermediate)

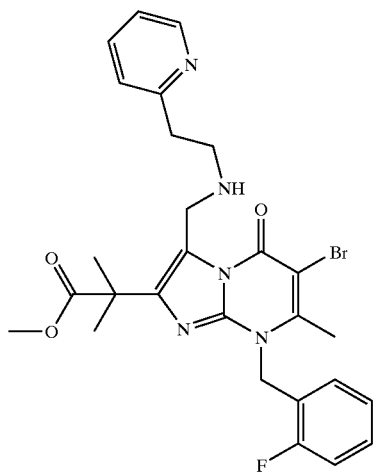

Step 4.1A 5-Bromo-6-methyl-2-(1-methoxycarbonyl-1-methylethyl)-7H-imidazolo[1,2-a]pyrimid-4-one Under nitrogen atmosphere, to a solution of 2-amino-5-bromo-4-hydroxy-6-methylpyrimidine (4.08 g, 20 mmol.) in dry DMF (80 ml), sodium hydride (800 mg, 20 mmol., 60% in mineral oil) was carefully added. The mixture was stirred at room temperature for 0.5 hour, followed by addition of methyl 4-bromo-2,2-dimethyl acetoacetate (20 mmol.). The mixture was then stirred at room temperature overnight. The resultant mixture was concentrated in vacuo, and the residue was dissolved in acetone (50 ml) and diluted with water (100 ml). Slowly concentration under reduced pressure resulted a precipitation. The solid was collected by filtration, washing with water, ether, and dried to yield the desired product; MS: 328 (M+H); proton NMR (CDCl$_3$): 1.64 (s, 6H), 2.55 (s, 3H), 3.77 (s, 3H), 7.40 (s, 1H).

Step 4.2B 5-Bromo-6-methyl-2-(1-methoxycarbonyl-1-methylethyl)-7-(2-fluorophenylmethyl)-imidazolo[1,2-a]pyrimid-4-one To a solution of 5-bromo-6-methyl-2-(1-methoxycarbonyl-1-methylethyl)-7H-imidazolo[1,2-a]pyrimid-4-one (2.4 mmol.) in DME (5 ml), tetrabutylammonium fluoride (4 ml, 1.0 M in THF) was added and followed by addition of 2-fluorobenzyl bromide (0.45 ml, 1.5 eq.). The mixture was stirred at room temperature overnight and then concentrated and purified by silica gel chromatography (hexane/ethyl acetate) to give the desired product as a white powder; MS: 436 (M+H); NMR (CDCl$_3$, δ): 1.59 (s, 6H), 2.60 (s, 3H), 3.64 (s, 3H), 5.68 (s, 2H), 7.00–7.38 (m, 4H), 7.51 (s, 1H).

Step 4.1C 3-{N-[2-(2-Pyridyl)ethyl]aminomethyl}-5-bromo-6-methyl-2-(1-methoxycarbonyl-1-methylethyl)-7-(2-fluorophenylmethyl)-imidazolo[1,2-a]pyrimid-4-one To a solution of 2-(2-pyridyl)ethylamine (12 mg, 0.1 mmol.) and aqueous formaldehyde (0.01 ml) in acetic acid (1 ml), 5-bromo-6-methyl-2-(1-methoxycarbonyl-1-ethylethyl)-7-(2-fluorophenylmethyl)-imidazolo[1,2-a]pyrimid-4-one (22 mg, 0.05 mmol.) was added. The solution was stirred at room temperature for 1 hours and directly purified by prep HPLC to give the product; MS: 570 (M+H).

EXAMPLE 4.2

Synthesis of 2-(1-methoxycarbonyl-1-methylethyl)-3-(N-methyl-N-benzylaminomethyl)-5-(3-methoxyphenyl)-6-methyl-7-(2-flurorbenzyl) imidazolo[1,2-a]pyrimid-4-one

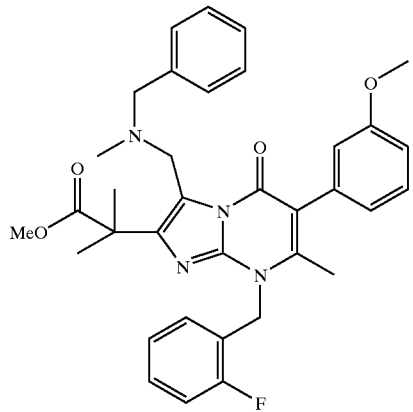

Step 4.2A 2-(1-Methoxycarbonyl-1-methylethyl)-5-(3-methoxyphenyl)-6-methyl-7-(2-fluorobenzyl) imidazolo[1,2-a]pyrimid-4-one Into a mixture of 2-(1-methoxycarbonyl-1-methylethyl)-5-(bromo)-6-methyl-7-(2-fluorobenzyl)imidazolo[1,2-a]pyrimid-4-one (200 mg, 458 μmol), 3-methoxyphenylboronic acid (139 mg, 916 μmol), potassium carbonate (190 mg, 1.4 mmol) in toluene (4 ml) and $H_2O$ (2 ml) were added under $N_2$ tetrakis(triphenylphosphine)palladium(0) (26 mg, 23 μmol). The resulting solution was stirred and refluxed in a ChemGlass pressure tube under $N_2$ for 2.5 hours. The solution was extracted with EtOAc and purified using Flash silica chromatography (hexane to hexane/EtOAc, 7/3) to give the desired product as an ecru solid in 83% yield; MS: 464 (M+H).

Step 4.2B 2-(1-Methoxycarbonyl-1-methylethyl)-3-(N-methyl-N-benzylaminomethyl)-5-(3-methoxyphenyl)-6-methyl-7-(2-fluorobenzyl) imidazolo[1,2-a]pyrimid-4-one 2-(1-Methoxycarbonyl-1-methylethyl)-5-(3-methoxyphenyl)-6-methyl-7-(2-fluorobenzyl)imidazolo[1,2-a]pyrimid-4-one (17.7 mg, 38 μmol) was added to a stirring solution of aqueous formaldehyde (one drop) and N-methylbenzylamine (0.1 ml, 775 μmol) in acetic acid (1 ml), and then stirred at room temperature overnight. The solution was dried under $N_2$, made basic with $NaHCO_3$, extracted with dichloromethane and purified using prep silica TLC (hexane/EtOAc, 6/4) to give the product as an oil in 94% yield. $H^1$-NMR ($CDCl_3$): 1.69(s,6H), 2.07(s,3H), 2.16(s,3H), 3,58(s, 2H), 3.61(s,3H), 3.81(s,3H), 4.26(s,2H), 5.61(s,2H), 6.75(m,13H).

Following a procedure similar to that described above, the following compounds were prepared:

| Example | $R_1NR_2$ | Q—Ar | MS (M + H)+ |
|---|---|---|---|
| 4A | BnNMe | 3-OMe—Ph | 597 |
| 4B | 2-PyCH₂CH₂NMe | 3-OMe—Ph | 611 |
| 4C | PhCH₂CH₂NMe | 3-OMe—Ph | 612 |
| 4D | 2-FuranCH₂NMe | 3-OMe—Ph | 587 |
| 4E | (4-benzylpiperidinyl) | 3-OMe—Ph | 651 |
| 4F | (bis(4-fluorophenyl)methylpiperazinyl) | 3-OMe—Ph | 763 |
| 4G | 2-PyCH₂NH | 3-OMe—Ph | 584 |
| 4H | 2-PyCH₂CH₂NMe | 2-F-3-OMePh | 630 |

EXAMPLE 5

Synthesis of 2-Ethoxycarbonylmethyl-3-{N-methyl-N-[2-(2-pyridyl)ethyl]aminomethyl}-5-(3-methoxyphenyl)-6-methyl-7-(2-fluorobenzyl) imidazolo[1,2-a]pyrimid-4-one

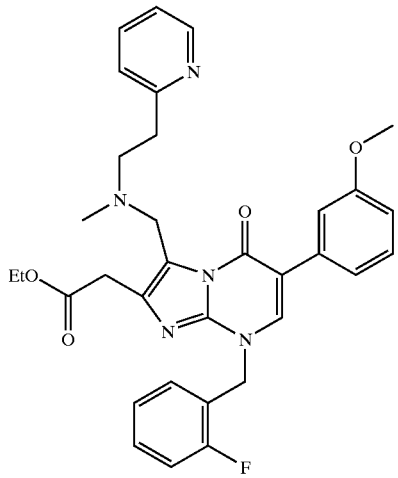

Step 5A 2-Ethoxycarbonylmethyl-5-bromo-6-methyl-7H-imidazolo[1,2-a]pyrimid-4-one A solution of 2-amino-5-bromo-6-methylpyrimid-4-one (8.16 g, 40 mmol.) in DMF (30 ml) was cooled down with ice-water bath. NaH (60% in oil, 1.76 g, 44 mmol.) was added in portions and the reaction mixture stirred at 0° C. for 30 min and then warmed to ambient temperature for 1 h. Ethyl 4-chloroacetoacetate (6.91 g, 42 mmol) in 50 ml DMF was added dropwise in 3 h and the reaction mixture was stirred at ambient temperature overnight. Reaction mixture was quenched with saturated $NH_4Cl/H_2O$, and precipitates were filtered. The filtrate was concentrated in vacuo and the residue was partitioned between water and dichloromethane. The aqueous phase was extracted with dichloromethane (3×100 ml). The organic phases were combined, dried over sodium sulfate and concentrated to give the tilted compound (3.05 g, 24%); MS 314 $(M+H)^+$.

Step 5B 2-Ethoxycarbonylmethyl-5-bromo-6-methyl-7-(2-fluorobenzyl)-imidazolo[1,2-a]pyrimid-4-one A solution of 2-ethoxycarbonylmethyl-5-bromo-6-methyl-7H-imidazolo[1,2-a]pyrimid-4-one, (3.00 g, 9.55 mmol.) in DME (35 ml) was treated with 1M TBAF/THF (14.3 mL, 14.3 mmol.) and stirred at ambient temperature for 30 min. 2-Fluorobenzyl bromide (2.71 g, 14.3 mmol.) was introduced. The reaction mixture was stirred at ambient temperature overnight, concentrated in vacuo, and the residue was purified by flash chromatography (silica, 40% EtOAc/hexanes) to give the designed compound (356 mg, 9%). MS 424 $(M+H)^+$.

Step 5C 2-Ethoxycarbonylmethyl-5-(3-methoxyphenyl)-6-methyl-7-(2-fluorobenzyl) imidazolor[1,2-a]pyrimid-4-one 2-Ethoxycarbonylmethyl-5-bromo-6-methyl-7-(2-fluorobenzyl)imidazolo[1,2-a]pyrimid-4-one (190 mg, 0.45 mmol.) in benzene/water (8 ml/5 ml) was added $K_2CO_3$ (155 mg, 1.12 mmol.), 3-methoxyphenylboronic acid (86 mg, 0.56 mmol.), and tetrakis(triphenylphosphine)palladium(0) (52 mg, 0.045 mmol.). The reaction mixture was deoxygenated with $N_2$ and heated at 90° C. for 16 h. The reaction mixture was partitioned between brine and EtOAc. The organic layer was dried (sodium sulfate), evaporated, purified by flash chromatography (silica, 45% EtOAc/hexane) to give the title compound. (93 mg, 46%); MS 450 $(M+H)^+$.

Step 5D 2-Ethoxycarbonylmethyl-3-{N-methyl-N-[2-(2-pyridyl)ethyl]aminomethyl}-5-(3-methoxyphenyl)-6-methyl-7-(2-fluorobenzyl) imidazolo[1,2-a]pyrimid-4-one A mixture of aqueous formaldehyde (37%, 1 drop) and amine (1 drop) in acetic acid (1.5 ml) was added 2-ethoxycarbonylmethyl-5-(3-methoxyphenyl)-6-methyl-7-(2-fluorobenzyl)imidazolo[1,2-a]pyrimid-4-one (20 mg, 0.045 mmol.) and the reaction mixture was stirred at ambient temperature for 12 h. The solvent was evaporated and the residue was partitioned between dichloromethane and saturated $NaHCO_3$/water, the organic layer was dried (sodium sulfate), evaporated and purified by prep. TLC (silica, 5% MeOH/dichloromethane) to give the titled compound; MS 598 $(M+H)^+$.

Replacing 2-(2-pyridyl)ethyl at the $R_1$ position with benzyl, gave 2-ethoxycarbonylmethyl-3-{N-methyl-N-benzyl}-5-(3-methoxyphenyl)-6-methyl-7-(2-fluorobenzyl) imidazolo[1,2-a]pyrimid-4-one. MS 583 $(M+H)^+$; $H^1$-NMR ($CDCl_3$): 1.23 (t,3H), 2.15 (s,3H), 2,47 (s,3H), 3.79 (s,2H), 3.83 (2,2H), 3.87 (s,3H), 4.14 (q, 2H), 4.30 (s,2H), 5.62 (s,2H), 6.78–7.65 (m,13H).

Following a procedure similar to that described above, the following compounds were prepared:

| Example | $R_1NR_2$ | MS (M + H) |
|---|---|---|
| 5A | 2-PyCH$_2$CH$_2$NMe | 598 |
| 5B | BnNMe | 583 |
| 5C | BuNMe | 549 |
| 5D | ⸹—N⟨⟩—Bn (piperidine-Bn) | 637 |
| 5E | ⸹—N⟨⟩N— (piperazine) | 562 |

It will be appreciated that, although specific embodiments of the invention have been described herein for purposes of illustration, various modifications may be made without departing from the spirit and scope of the invention. Accordingly, the invention is not limited except as by the appended claims.

We claim:

1. A compound having the following structure:

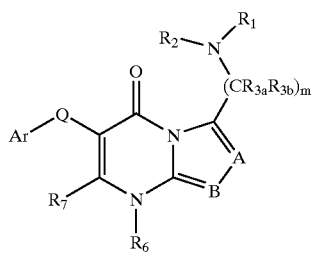

or a stereoisomer or pharmaceutically acceptable salt thereof, wherein:

A is N or $CR_4$;

B is N or $CR_5$;

Q is a direct bond or —$(CR_{8a}R_{8b})_r$—Z—$(CR_{10a}R_{10b})_s$—;

m, r and s are the same or different and selected from 0 to 6;

Z is a direct bond or —O—, —S—, —$NR_9$—, —SO—, —$SO_2$—, —$OSO_2$—, —$SO_2O$—, —$SO_2NR_9$—, —$NR_9SO_2$—, —CO—, —COO—, —OCO—, —$CONR_9$—, —$NR_9CO$—, —$NR_9CONR_{9a}$—, —$OCONR_9$— or —$NR_9COO$—;

$R_1$ is hydrogen, alkyl, substituted alkyl, aryl, substituted aryl, arylalkyl, substituted arylalkyl, heteroaryl, substituted heteroaryl, heteroarylalkyl, substituted heteroarylalkyl, —$C(R_{1a})(=NR_{1b})$ or —$C(NR_{1a}R_{1c})(=NR_{1b})$;

$R_2$ is hydrogen, alkyl or substituted alkyl;

or $R_1$ and $R_2$ taken together with the nitrogen atom to which they are attached form heterocycle or substituted heterocycle;

$R_{3a}$ and $R_{3b}$ are independently selected from hydrogen, alkyl, substituted alkyl, aryl, substituted aryl, arylalkyl, heterocycle, heterocyclealkyl, hydroxy, alkoxy, alkylthio, alkylamino, $CONR_{14}R_{15}$ or —$COOR_{14}$;

or $R_{3a}$ and $R_{3b}$ taken together with the carbon atom to which they are attached form a 3–6 membered homocycle, substituted homocycle, heterocycle or substituted heterocycle;

or $R_{3a}$ and $R_{3b}$ taken together form $=NR_{3c}$;

$R_4$ is hydrogen, halogen, cyano, nitro, alkyl, substituted alkyl, arylalkyl, substituted arylalkyl, heterocyclealkyl, substituted heterocyclealkyl, —$COR_{11}$, —$COOR_{11}$, —$CONR_{12}R_{13}$, —$OR_{11}$, —$OCOR_{11}$, —$OSO_2R_{11}$, —$SR_{11}$, —$SO_2R_{11}$, —$NR_{12}R_{13}$, —$NR_{11}COR_{12}$, —$NR_{11}CONR_{12}R_{13}$, —$NR_{11}SO_2R_{12}$ or —$NR_{11}SO_2NR_{12}R_{13}$;

$R_5$ is hydrogen, halogen, lower alkyl, arylalkyl, alkoxy, alkylthio, alkylamino, cyano or nitro;

$R_6$ is hydrogen, alkyl, substituted alkyl, aryl, substituted aryl, arylalkyl, substituted arylalkyl, heteroaryl, substituted heteroaryl, heteroarylalkyl or substituted heteroarylalkyl;

$R_7$ is hydrogen, halogen, cyano, alkyl, substituted alkyl, alkoxy, alkylthio, alkylsulfonyl or alkylamino;

Ar is aryl, heteroaryl, substituted aryl or substituted heteroaryl; and $R_{1a}$, $R_{1b}$, $R_{1c}$, $R_{3c}$, $R_{8a}$, $R_{8b}$, $R_9$, $R_{9a}$, $R_{10a}$, $R_{10b}$, $R_{11}$, $R_{12}$, $R_{13}$ and $R_{14}$ are the same or different and at each occurrence independently hydrogen, alkyl, substituted alkyl, aryl, substituted aryl, arylalkyl, substituted arylalkyl, heterocycle, substituted heterocycle, heterocyclealkyl or substituted heterocyclealkyl;

or $R_{1a}$ and $R_{1b}$, $R_{8a}$ and $R_{8b}$, $R_{10a}$ and $R_{10b}$, or $R_{12}$ and $R_{13}$ taken together with the atom or atoms to which they are attached form homocycle, substituted homocycle, heterocycle or substituted heterocycle.

2. The compound of claim 1 wherein Q is a direct bond and having the following structure:

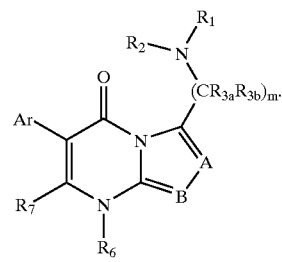

3. The compounds of claim 1 wherein Q is —$(CR_{8a}R_{8b})_r$—Z—$(CR_{10a}R_{10b})_s$—.

4. The compound of claim 3 wherein r is zero.

5. The compound of claim 3 wherein s is zero.

6. The compound of claim 3 wherein Z is carbonyl.

7. The compound of claim 2 wherein A is $CR_4$, B is nitrogen and having the following structure:

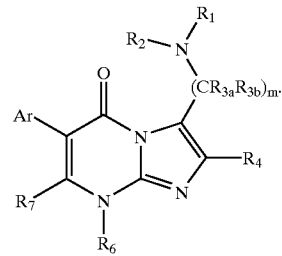

8. The compound of claim 2 wherein A is $CR_4$, B is $CR_5$ and having the following structure:

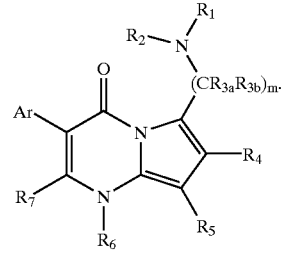

9. The compound of claim 2 wherein A is N, B is $CR_5$ and having the following structure:

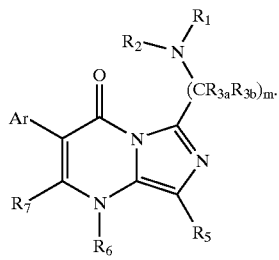

10. The compound of claim 2 wherein A is N, B is N and having the following structure:

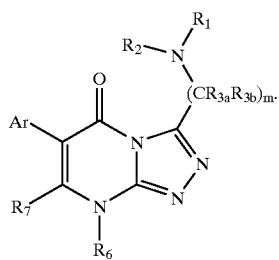

11. The compound of claim 1 wherein $R_6$ is arylalkyl or substituted arylalkyl.
12. The compound of claim 11 wherein $R_6$ is benzyl or substituted benzyl.
13. The compound of claim 1 wherein $R_7$ is alkyl.
14. The compound of claim 13 wherein $R_7$ is methyl.
15. The compound of claim 1 wherein $R_5$ is hydrogen.
16. The compound of claim 1 wherein $R_5$ is halogen, nitro or cyano.
17. The compound of claim 1 wherein $R_4$ is alkyl or substituted alkyl.
18. The compound of claim 1 wherein $R_{3a}$ and $R_{3b}$ are both hydrogen.
19. The compound of claim 1 wherein m is 1.
20. The compound of claim 1 wherein $R_2$ is alkyl.
21. The compound of claim 1 wherein $R_1$ is arylalkyl, substituted arylalkyl, heteroarylalkyl or substituted heteroarylalkyl.
22. The compound of claim 21 wherein $R_1$ is benzyl or substituted benzyl.
23. The compound of claim 21 wherein $R_1$ is —$CH_2$(heteroalkyl) or —$CH_2CH_2$(heteroaryl).
24. The compound of claim 1 where $R_1$ and $R_2$ taken together with the nitrogen to which they are attached form heterocycle or substituted heterocycle.
25. The compound of claim 1 wherein the compound is:

3-(N-Benzyl-N-methyl)aminomethyl-2-(tert-butyl)-6-methyl-7-(2-fluorobenzyl)-5-(3-methoxyphenyl)imidazolo[1,2-a]pyrimid-4-one;
3-(N-(2-Pyridylmethyl))aminomethyl-2-(tert-butyl)-6-methyl-7-(2-fluorobenzyl)-5-(3-methoxyphenyl)imidazolo[1,2-a]pyrimid-4-one;
3-(N-(2-Pyridylmethyl)-N-methyl)aminomethyl-2-(tert-butyl)-6-methyl-7-(2-fluorobenzyl)-5-(3-methoxyphenyl)imidazolo[1,2-a]pyrimid-4-one;
3-[N-Methyl-N-(2-pyridylethyl)]aminomethyl-2-(tert-butyl)-6-methyl-7-(2-fluorobenzyl)-5-(3-methoxyphenyl)imidazolo[1,2-a]pyrimid-4-one;
3-[N-(2-Furanmethyl)-N-methyl]aminomethyl-2-(tert-butyl)-6-methyl-7-(2-fluorobenzyl)-5-(3-methoxyphenyl)imidazolo[1,2-a]pyrimid-4-one;
3-[N-Methyl-N-(2-pyridylethyl)]aminomethyl-2-(ethoxycarbonylmethyl)-6-methyl-7-(2-fluorobenzyl)-5-(3-methoxyphenyl)imidazolo[1,2-a]pyrimid-4-one;
1-(N-Benzyl-N-methyl)aminomethyl-2-(tert-butyl)-4-(2-fluorobenzyl)-6-(3-phenylpropylaminocarbonyl)pyrrolo[1,2-a]pyrimid-7-one;
1-[(N-Methyl-N-(2-pyridylethyl)]aminomethyl-2-(tert-butyl)-4-(2-fluorobenzyl)-6-(3-phenylpropylaminocarbonyl)pyrrolo[1,2-a]pyrimid-7-one;
1-[(N-Methyl-N-(2-pyridylethyl)]aminomethyl-2-(tert-butyl)-4-(2-fluorobenzyl)-5-methyl-6-(3-methoxyphenyl)pyrrolo[1,2-a]pyrimid-7-one;
3-(N-Benzyl-N-methyl)aminomethyl-2-(t-butyl)-4-(2-fluorobenzyl)-5-methyl-6-(3-methoxyphenyl)imidazolo[3,4-a]pyrimid-7-one;
1-[N-Methyl-N-(2-pyridylethyl)]aminomethyl-4-(2-fluorobenzyl)-5-methyl-6-(3-methoxyphenyl)imidazolo[3,4-a]pyrimid-7-one;
1-[N-(2-Furanmethyl)-N-methyl]aminomethyl-4-(2-fluorobenzyl)-5-methyl-6-(3-methoxyphenyl)imidazolo[3,4-a]pyrimid-7-one;
3-(N-Benzyl-N-methyl)aminomethyl-6-methyl-7-(2-fluorobenzyl)-5-(3-methoxyphenyl)-1,2,4-triazolo[4,3-a]pyrimid-4-one;
3-[N-Methyl-N-(2-pyridylethyl)]aminomethyl-6-methyl-7-(2-fluorobenzyl)-5-(3-methoxyphenyl)-1,2,4-triazolo[4,3-a]pyrimid-4-one;
3-[N-(2-Furanmethyl)-N-methyl]aminomethyl-6-methyl-7-(2-fluorobenzyl)-5-(3-methoxyphenyl)-1,2,4-triazolo[4,3-a]pyrimid-4-one;
1-(N-Benzyl-N-methyl)aminomethyl-2-(1-methoxycarbonyl-1-methylethyl)-7-(2-fluorobenzyl)-6-methyl-5-(3-methoxyphenyl)imidazolo[1,2-a]pyrimid-4-one; or
1-[N-(2-Pyridylethyl)-N-methyl]aminomethyl-2-(1-methoxycarbonyl-1-methylethyl)-7-(2-fluorobenzyl)-6-methyl-5-(3-methoxyphenyl)imidazolo[1,2-a]pyrimid-4-one.

26. A pharmaceutical composition comprising a compound of claim 1 and a pharmaceutically acceptable carrier or diluent.

27. A method for treating prostatic cancer, uterine cancer, breast cancer, or pituitary gonadotroph adenomas of a subject in need thereof, comprising administering to the subject an effective amount of the pharmaceutical composition of claim 26.

28. A method for treating endometriosis, polycystic ovarian disease, uterine fibroids, or precocious puberty of a subject in need thereof, comprising administering to the subject an effective amount of the pharmaceutical composition of claim 26.

29. A method for preventing pregnancy of a subject in need thereof, comprising administering an effective amount of the pharmaceutical composition of claim 26.

30. A method for treating irritable bowel syndrome, premenstrual syndrome, hirsutism, or short stature of a subject in need thereof, comprising administering to the subject an effective amount of the pharmaceutical composition of claim 26.

* * * * *

UNITED STATES PATENT AND TRADEMARK OFFICE
CERTIFICATE OF CORRECTION

PATENT NO. : 6,537,998 B1  
DATED : March 25, 2003  
INVENTOR(S) : Yun-Fei Zhu et al.

It is certified that error appears in the above-identified patent and that said Letters Patent is hereby corrected as shown below:

Column 65,
Line 46, "(heteroalkyl)" should be corrected to read as -- (heteroaryl) --.

Signed and Sealed this

First Day of July, 2003

JAMES E. ROGAN
*Director of the United States Patent and Trademark Office*